US012770765B2

(12) United States Patent
Luo et al.

(10) Patent No.: US 12,770,765 B2
(45) Date of Patent: Oct. 20, 2026

(54) SUPERPARAMAGNETIC MONODISPERSE PARTICLES AND METHOD FOR THE PRODUCTION THEREOF

(71) Applicant: N-lab Technology Center Pte. Ltd., Singapore (SG)

(72) Inventors: He-Kuan Luo, Singapore (SG); Honglei Wang, Singapore (SG); Kelei Chen, Singapore (SG)

(73) Assignee: N-lab Technology Center Pte. Ltd., Singapore (SG)

(*) Notice: Subject to any disclaimer, the term of this patent is extended or adjusted under 35 U.S.C. 154(b) by 1022 days.

(21) Appl. No.: 17/997,891

(22) PCT Filed: Apr. 29, 2021

(86) PCT No.: PCT/SG2021/050236
§ 371 (c)(1),
(2) Date: Nov. 3, 2022

(87) PCT Pub. No.: WO2021/225519
PCT Pub. Date: Nov. 11, 2021

(65) Prior Publication Data
US 2023/0352218 A1 Nov. 2, 2023

Related U.S. Application Data

(60) Provisional application No. 63/020,755, filed on May 6, 2020.

(51) Int. Cl.
*H01F 1/00* (2006.01)
*G01N 33/543* (2006.01)
*H01F 1/06* (2006.01)

(52) U.S. Cl.
CPC ..... *H01F 1/0054* (2013.01); *G01N 33/54326* (2013.01); *G01N 2446/20* (2013.01); *G01N 2446/84* (2013.01)

(58) Field of Classification Search
CPC .... H01F 1/0054; H01F 1/0018; H01F 1/0045; H01F 1/032; H01F 1/061; H01F 1/11;
(Continued)

(56) References Cited

U.S. PATENT DOCUMENTS 4,654,267 A 3/1987 Ugelstad et al.
5,091,206 A 2/1992 Wang et al.
(Continued)

FOREIGN PATENT DOCUMENTS

CN 106040309 A 10/2016
CN 108467461 A 8/2018
(Continued)

OTHER PUBLICATIONS

Machine translation of JP2006265290A (Year: 2006).*
(Continued)

*Primary Examiner* — Matthew E. Hoban
*Assistant Examiner* — Lynne Edmondson
(74) *Attorney, Agent, or Firm* — Osha Bergman Watanabe & Burton LLP

(57) ABSTRACT

Disclosed herein are monodisperse superparamagnetic beads, having a core-shell structure, and a method for preparing the beads.

20 Claims, 6 Drawing Sheets

(58) Field of Classification Search
CPC . G01N 2446/20; G01N 2446/84; B01J 13/22; B01J 13/14; C08F 285/00; C08F 292/00
See application file for complete search history.

(56) References Cited

U.S. PATENT DOCUMENTS

| | | | |
|---|---|---|---|
| 7,713,627 | B2 | 5/2010 | Tamori et al. |
| 2004/0101564 | A1 | 5/2004 | Rioux et al. |
| 2005/0129775 | A1 | 6/2005 | Lanphere et al. |
| 2009/0092837 | A1 | 4/2009 | Axen et al. |
| 2017/0218095 | A1 | 8/2017 | Modahl et al. |

FOREIGN PATENT DOCUMENTS

| | | | |
|---|---|---|---|
| CN | 110187116 | A | 8/2019 |
| JP | 2002348308 | A | 12/2002 |
| JP | 2004205481 | A | 7/2004 |
| JP | 3627342 | B2 | 3/2005 |
| JP | 2006265290 | A | 10/2006 |
| JP | 2007127426 | A | 5/2007 |
| JP | 2007527454 | A | 9/2007 |
| JP | 2008081647 | A | 4/2008 |
| JP | 4593146 | B2 | 12/2010 |
| WO | 2017164822 | A1 | 9/2017 |

OTHER PUBLICATIONS

Gu et al., "Facile one-pot synthesis of multi-armed Fe3O4 nanocrystals", Journal of Alloys and Compounds 472 (2009) 50-54 (Year: 2009).*

Office Action issued in counterpart Japanese Patent Application No. 2022-567337 mailed on Feb. 18, 2025 (9 pages).

International Preliminary Report on Patentability issued in International Application No. PCT/SG2021/050236 dated Nov. 17, 2022 (9 pages).

Database WPI Week 201974 Thomson Scientific, London, GB; AN 2019-75944D XP002803595 (2 pages).

Yan, Xingru et al. "Magnetic Polystyrene Nanocomposites Reinforced with Magnetite Nanoparticles" Magnetic Polystyrene Nanocomposites, Macromolecular Materials and Engineering., vol. 299, No. 4, Apr. 1, 2014 (Apr. 1, 2014), pp. 485-494, XP055822699 (12 pages).

Database WPI Week 201714 Thomson Scientific, London, GB; AN 2016-683709 XP002803596 (2 pages).

Miao, Lei et al. "Superparamagnetic-Oil-Filled Nanocapsules of a Ternary Graft Copolymer" Langmuir, vol. 30, No. 14, Apr. 15, 2014 (Apr. 15, 2014), pp. 3996-4004, XP055822698 (9 pages).

Philippova, Olga et al. "Magnetic polymer beads: Recent trends and developments in synthetic design and applications" European Polymer Journal 47 (2011 ) 542-559 (18 pages).

Kniajanski, Sergei et al. "Synthesis of Highly Loaded and Well-Controlled Magnetic Beads via Emulsion Polymerization" J. Appl. Polym. Sci. 2012 (8 pages).

Kai, Jiang et al. "Synthesis of monodisperse crosslinked polystyrene microspheres" Pet. Sci. (2008) 5: 375-378 (4 pages).

Cui, Longlan et al. Developing a Hybrid Emulsion Polymerization System to Synthesize Fe3O4/Polystyrene Latexes with Narrow Size Distribution and High Magnetite Content Journal of Polymer Science: Part A: Polymer Chemistry, vol. 45, 5285-5295 (2007) (11 pages).

Lee, Ki-Chang et al. "Highly Crosslinked Micron-Sized, Monodispersed Polystyrene Particles by Semicontinuous Dispersion Polymerization. II. Semicontinuous, Delayed Addition and Seeded Semicontinuous Processes" Journal of Applied Polymer Science, vol. 115, 3092-3102 (2010) (11 pages).

International Search Report issued in International Application No. PCT/SG2021/050236 dated Jul. 23, 2021 (4 pages).

Written Opinion issued in International Application No. PCT/SG2021/050236 dated Jul. 23, 2021 (7 pages).

* cited by examiner

SUPERPARAMAGNETIC MONODISPERSE PARTICLES AND METHOD FOR THE PRODUCTION THEREOF

FIELD OF INVENTION

This invention relates to monodisperse superparamagnetic beads useful for in-vitro diagnostic (IVD) assays and other applications, as well as methods of manufacturing said beads.

BACKGROUND

Monodisperse superparamagnetic beads are widely used in the in vitro diagnostic (IVD) and biotechnology fields. For example, in chemiluminescence assays, monodisperse superparamagnetic beads are applied to quantify the amount of an antigen or antibody present in a sample through a magnetically tagged antibody or antigen. Monodisperse superparamagnetic beads are also commonly used materials in diagnostic kits for nucleic acid (DNA and RNA) extraction before polymerase chain reaction (PCR). Easily adapted to automated processes, these beads are used on more than 25,000 routine IVD instruments worldwide. Monodisperse superparamagnetic beads also are finding uses in antibody purification and the isolation of a wide range of specific mammalian cells, bacteria, viruses, subcellular organelles, and individual proteins. Monodisperse superparamagnetic beads are powerful tools for antibody purification and isolation due to their superparamagnetic properties and their ability to be enriched with affinity groups (e.g. Streptavidin) on their surfaces. A typical procedure for isolation involves mixing a suspension of the monodisperse superparamagnetic beads with a solution containing the target molecule (e.g. a biotin-labelled antibody) or cell. After an incubation period, the target will bind to the affinity ligand and a powerful magnet is then used to capture the magnetic beads and their trapped target molecules or cells. The unbound materials or impurities are then removed by aspiration and the bound materials are washed for downstream application. Due to their ability to aid the rapid development of the IVD and biotechnology fields, monodisperse superparamagnetic beads have attracted significant attention in recent years.

The monodisperse magnetic beads are a combination of magnetic particles and polymeric material(s). The beads benefit from the combination of properties inherently provided by these components. The magnetic property of the beads (arising from the magnetic particles) allows for the rapid and easy separation of the beads by the application of an external magnetic field. The polymeric material(s) stabilizes the magnetic particles, reduces the density of the beads, offers better dispersal of beads in a range of fluid buffers, and endows the particles with functional groups that can be used to enable the desired applications in immunoassay methodologies, in the isolation of nucleic acid sequences, cells and microorganisms etc., through the attachment of active moieties through these functional groups. For a review of the applications of these beads, and their functionalisation, see European Polymer Journal 2011, 47, 542-559.

Monodisperse superparamagnetic beads (typically 1-5 microns diameter) are commonly used as a powerful tool for in-vitro diagnostic (IVD) applications (see ibid for review article that discusses these applications). The good uniformity in size, shape, and surface area is critical for reproducibility in biological systems and minimizes chemical agglutinations during the separation process. Thus, the discovery of monodisperse polymer beads with superparamagnetic properties has significantly promoted the IVD industry globally over the past ten years, and it is expected that this industry will continue growing quickly over the next decade.

Magnetic beads usually have three types of different structures (FIG. 1, types I to III). The type I structure has magnetic nanoparticles (NPs) distributed throughout the polymeric material matrix; the type II structure has a core-shell structure, with a shell formed of magnetic NPs on the surface of the bead, with a polymeric core; and the type III structure has a polymeric shell with a core containing the magnetic NPs. Additionally, it is noted that the type III structure tends to have poor superparamagnetic properties because the magnetic core is generally too big, such that the magnetic NPs may interfere with one another, thereby reducing the superparamagnetic properties of the bead. However, simply selecting one of these designs will not result in superparamagnetic properties. In order to have optimal superparamagnetic properties, the beads should be loaded with magnetic NPs having a size of from 5-15 nm. Thus, the type I to III composite beads illustrated in FIG. 1 will only be superparamagnetic when the magnetic NPs fall within this size range.

To achieve the type I design discussed above, there are two synthetic strategies, which are discussed below.

The first strategy is to synthesize superparamagnetic $Fe_3O_4$ NPs, which are then dispersed into an emulsion polymerization system of styrene to encapsulate the NPs into the polystyrene beads [e.g. see: US20090092837, Journal of Applied Polymer Science 2013, DOI: 10.1002/APP.38857 (1726-1733), Journal of Polymer Science: Part A: Polymer Chemistry, 2007, 45, 5285-5295]. However, this synthetic strategy has two problems. The first problem is that it can only produce superparamagnetic polystyrene beads having a small diameter, usually between 100-200 nm, which is too small for IVD applications. The second problem is that the superparamagnetic $Fe_3O_4$ NPs are not evenly distributed throughout the polystyrene beads, thus different beads contain a different number of superparamagnetic $Fe_3O_4$ NPs. As a result, the magnetic response of the magnetic spheres will have a wide distribution, which is undesirable for IVD applications. In addition, because of the nature of the styrene emulsion polymerization, these two problems have not been possible to overcome so far. Similar encapsulation strategies have also been applied to prepare type III magnetic beads.

The second strategy to synthesize type I monodisperse superparamagnetic beads is to synthesize monodisperse polymer beads as a carrier for superparamagnetic NPs first, then upload superparamagnetic $Fe_3O_4$ NPs. In this synthetic strategy, the first step is to synthesize highly monodisperse polymer beads which meet at least three requirements:

(1) the polymer beads are highly monodisperse with a reproducible diameter, such as 1.0 micron;
(2) the polymer beads are cross-linked, thus have good stiffness and tolerance to organic solvents; and
(3) the polymer beads are functionalized to facilitate the on-site generation of superparamagnetic $Fe_3O_4$ nanoparticles.

To realize the above requirements, complicated and costly procedures are used in the state-of-the-art synthetic techniques. For example, US 20170218095 (Ugelstad process) discloses a three-step procedure to produce porous and functionalized polystyrene beads that are used for the production of superparamagnetic polymer beads. The first step is the synthesis of polystyrene seeds of low molecular weight via an emulsion polymerisation method. Sodium dodecyl sulfate (SDS) was used as a surfactant, ammonium persulfate (APS) was used as initiator and borax was used to increase ionic strength. Styrene was extracted with 10 wt % sodium hydroxide to remove stabilizer (4-tert-butylcatechol), which can inhibit the polymerization of styrene. The resulting monodisperse polystyrene seeds particle have a diameter ranging from 50 to 200 nm. The second step is active swelling and cross-linking. The polystyrene seeds were swelled for 24 hours at 25° C. with an initiator emulsion comprising dioctanoyl peroxide, SDS and acetone. The swelled seeds were then mixed with a monomer emulsion comprising toluene, DVB, styrene, PVP, SDS and water, and the temperature increased to 60° C. to trigger the crosslinking polymerization, which was run for 2 hours, affording porous and cross-linked polystyrene beads. The third step is the functionalization of the porous and cross-linked beads by nitration of the phenyl rings in the beads with mixture of sulfuric acid and nitric acid (65%) to introduce $NO_2$ groups to these polystyrene spheres (U.S. Pat. No. 4,654,267). The nitrated beads are used for the subsequent magnetisation step with ammonia (25%) and iron (II) sulfate heptahydrate. The authors demonstrated plenty of methods to introduce different functional groups by using different monomers in the second step in order to increase the iron content in the third step. However, the magnetic content for all options is below 15%. The only feasible method to improve iron content to above 15% is to use a nitration process to generate nitrated beads. The issue with this synthesis strategy is that it is time-consuming, with cumbersome operations to generate a well-controlled porous polystyrene support. Most importantly, to nitrify every 5 g of dry particles needs a mixture of concentrated nitric acid with 125 mL of concentrated sulfuric acid. Thus the process requires the large consumption of concentrated acids that are both oxidative and corrosive, which will cause severe environmental issues. In addition, to run this process on scale would also require stringent reactor and process controls.

The type II design may be obtained using the protocol of U.S. Pat. No. 7,713,627, which discloses a method to produce non-magnetic nuclear particles having a diameter of 1.5 μm. First, the primary large polystyrene beads were produced with a seeded emulsion polymerization of styrene with DVB at 75° C. for 8 hours using polystyrene beads of diameter 0.77 μm as seeds in an emulsion system containing di(3,5,5-trimethylhexanoyl) peroxide and SDS. The produced primary beads were then separated by centrifugation, washed with water, dried, and ground to afford the non-magnetic nuclear particles with an average diameter of 1.5 microns, which were then used to produce magnetic beads by loading ferrite-type fine magnetic material particles with a hydrophobilized surface (average primary particle diameter 0.01 μm). The magnetic NPs become attached to the surface of the spheres through hydrophobic interaction. The disadvantages of this process are: (1) the second step (grinding process) may not afford highly monodisperse beads and the beads may not have spherical shape; (2) the smallest beads demonstrated in this patent is 1.5 μm diameter. It appears that it could be difficult to generate smaller beads having 1.0 μm diameter or below; and (3) magnetic NPs only attach to the surface of the beads. Therefore, it will be difficult to achieve high magnetic or iron content because the outer surface area of the beads is limited and is determined by the polymer core diameter.

It has to be noted that cross-linked poly(styrene-DVB) beads can be produced by a one-pot two-stage polymerization process. In the first stage, polystyrene beads are formed in-situ, then DVB is added to form a core shell structure. Such a one-pot two-stage polymerization process can be carried out in an emulsion polymerization system or dispersion polymerization system. In an emulsion styrene polymerization system using sodium styrene sulfonate as surfactant and KPS as initiator, the obtained polymer beads have a diameter of about 200 nm (Petroleum Science, 2008, 5, 375-378). On the other hand, for a dispersion styrene polymerization system using PVP as stabilizer and AIBN as initiator in ethanol, the obtained polymer beads have a diameter of about 2.3 μm (Journal of Applied Polymer Science, 2010, 115, 3092-3102). Regardless of the difference on the size of the beads, in both cases, the obtained poly(styrene-DVB) beads are hydrophobic and so lack hydrophilic functional groups that can be used to upload superparamagnetic $Fe_3O_4$ NPs.

Therefore, there remains a need to develop a new synthetic strategy to produce spherical monodisperse polymer beads with tunable diameters, good stiffness and good tolerance to organic solvents, as well as containing enough hydrophilic functional groups to facilitate the upload of a high percentage of superparamagnetic $Fe_3O_4$ NPs, which enables the production of a new monodisperse superparamagnetic polymer beads with a diameter ranging 1-5 μm for IVD applications.

SUMMARY OF INVENTION

Aspects and embodiments of the invention are described in the following numbered clauses.

1. Monodisperse superparamagnetic beads, having a core-shell structure, said bead comprising:
   - a core portion formed from a polystyrene polymeric matrix material, where the polystyrene polymeric matrix material encapsulates a first batch of superparamagnetic $Fe_3O_4$ nanoparticles;
   - a first shell portion located directly on top of the core portion and formed from a crosslinked polymeric matrix material that is formed from a styrene monomer, a crosslinking monomer and a first functional monomer that has functional groups, where the copolymeric matrix material encapsulates a second batch of superparamagnetic $Fe_3O_4$ nanoparticles; and
     - a second shell portion located directly on top of the first shell portion, which is formed as a first layer, a second layer and a third layer,
   - the first layer comprises superparamagnetic $Fe_3O_4$ nanoparticles and a first layer polymeric matrix material that comprises a conjugating monomer and a bulk monomer;
   - a second layer extending beyond the first layer, which is formed from a second layer polymeric material that comprises a bulk monomer; and
   - a third layer on top of the second layer, which is formed from a third layer polymeric material that comprises a bulk monomer and a second functional monomer that has functional groups, wherein:
   - the superparamagnetic $Fe_3O_4$ nanoparticles in the first layer are directly bound to the functional groups present on an outer surface of the first shell portion;
   - the first layer polymeric matrix material surrounds the superparamagnetic $Fe_3O_4$ nanoparticles in the first layer; and
   - the second layer polymeric matrix material extends from the first layer polymeric matrix material and forms an outer surface of each monodisperse superparamagnetic bead.

2. The beads according to Clause 1, wherein the second and third layer polymeric matrix materials function to prevent the superparamagnetic magnetic nanoparticles from leaching out when the beads are placed into a solvent.

3. The beads according to Clause 1 or Clause 2, wherein the functional groups on the functional monomer in the first shell portion and the third layer of the second shell portion are independently selected from one or more of amino, carboxyl, epoxy, and hydroxyl, optionally wherein the functional groups on the functional monomer in the first shell portion and the second layer of the second shell portion are independently selected from a combination of hydroxyl and carboxyl groups or a combination of amino and carboxyl groups.

4. The beads according to any one of the preceding clauses, wherein the beads have a coefficient of variation based on their diameter of less than 15%, such as less than 10%, such as less than 5%.

5. The beads according to Clause 4, wherein the beads have a coefficient of variation based on their diameter of less than or equal to 2%.

6. The beads according to any one of the preceding clauses, wherein the beads have an average diameter of from 0.2 to 5.0 μm, such as from 0.5 to 4.0 μm.

7. The beads according to any one of the preceding clauses, wherein the polystyrene polymeric matrix material is formed from one or more of the group consisting of styrene, a styrene derivative, and copolymers thereof, optionally wherein the styrene derivative is selected from one or more of the group consisting of 4-methylstyrene, 3-methylstyrene, and 4-tertbutylstyrene.

8. The beads according to any one of the preceding clauses, wherein all of the superparamagnetic $Fe_3O_4$ nanoparticles in a bead account for from 10 to 80 wt %, such as from 20 to 70 wt %, such as from 30 to 50 wt % of the entire weight of each bead.

9. The beads according to Clause 8, wherein:

(a) the first batch of superparamagnetic $Fe_3O_4$ nanoparticles represents from 0.1 to 5 wt % of the entire weight of each bead; and/or (b) the second batch of superparamagnetic $Fe_3O_4$ nanoparticles represents from 0.5 to 10 wt % of the entire weight of each bead;

(c) the superparamagnetic $Fe_3O_4$ nanoparticles in the first layer of the second shell portion represent from 9.4 to 79.4 wt %, such as from 19.4 to 69.4 wt %, such as from 29.4 to 49.4 wt % of the entire weight of each bead.

10. The beads according to any one of the preceding clauses, wherein the crosslinking monomer is selected from one or more of the group consisting of divinylbenzene, ethylene glycol dimethylacrylate, bisphenol A dimethacrylate, butanediol dimethacrylate, tricyclodecane dimethanol diacrylate, pentaerythritol triacrylate, tripropylene glycol diacrylate, propoxylated neopentyl diacrylate, pentaerythritol triacrylate, ditrimethylolpropane tetraacrylate, dipentaerythritol pentaacrylate, dipentaerythritol penta/hexa-acrylate, tripropylene diacrylate, trimethylol propane ethoxylate triacrylate, trimethylol propane propoxylate triacrylate, di(trimethylolpropane)tetraacrylate, glycerol propoxylate triacrylate, pentaerythritol propoxylate triacrylate, poly(ethylene glycol) diacrylate, poly(propylene glycol) diacrylate, and tri(propylene glycol) diacrylate, optionally wherein the crosslinking monomer is selected from one or more of the group consisting of divinylbenzene, ethylene glycol dimethylacrylate, bisphenol A dimethacrylate, and N,N'-methylenebis(acrylamide).

11. The beads according to any one of the preceding clauses, wherein the first functional monomer is selected from one or more of the group consisting of acrylic acid, methacrylic acid, 2-carboxyethyl acrylate, acrylamide, methacrylamide, allylamine, (hydroxyethyl)methacrylate, hydroxypropyl methacrylate, 4-hydroxybutyl acrylate, glycidyl methacrylate, allyl glycidyl ether, 1,2-epoxy-5-hexene, maleic anhydride, 2-hydroxyethyl methacrylate, and 2-carboxyethyl acrylate oligomers.

12. The beads according to any one of the preceding clauses, wherein: the styrene monomer is selected from one or more of the group consisting of styrene, and a styrene derivative, optionally wherein the styrene derivative is selected from one or more of the group consisting of 4-methylstyrene, 3-methylstyrene, and 4-tertbutylstyrene.

13. The beads according to any one of the preceding clauses, wherein the first shell further comprises a first layer of a first polymeric matrix composition and a second layer of a second polymeric matrix composition, where:

the first layer is formed from a copolymer of a styrene monomer, a crosslinking monomer; and the second layer is formed from a copolymer a styrene monomer, a crosslinking monomer and a functional monomer.

14. The beads according to any one of the preceding clauses, wherein the superparamagnetic $Fe_3O_4$ nanoparticles have an average diameter of from 5 to 15 nm.

15. The beads according to any one of the preceding clauses, wherein:

(a) the weight to weight ratio of styrene groups to crosslinking groups in the core portion and first shell portion is from 20:1 to 1:2, such as from 10:1 to 1:1; and/or (b) the weight to weight ratio of styrene groups to functional groups in the core portion and first shell portion is from 20:1 to 1:2, such as from 10:1 to 1:1

16. The beads according to any one of the preceding clauses, wherein the $Fe_3O_4$ nanoparticles further comprise $Co_3O_4$ and/or $Mn_3O_4$ nanoparticles.

17. The beads according to any one of the preceding clauses, wherein the conjugating monomer is selected from one or more of the group consisting of methacryloyl chloride, 3-ethoxy-acryloyl chloride, acryloyl chloride, 4-pentenoyl chloride, methacrylic anhydride, 4-pentenoic anhydride, crotonic anhydride, valeric anhydride, 10-undecenoyl chloride, glycidol methacrylate, glycidol, and allyl glycidyl ether.

18. The beads according to any one of the preceding clauses, wherein the bulk monomer is selected from one or more of a polyether monomer, a polyester monomer, a polyacrylamide monomer, and a polyacid monomer, optionally wherein the bulk monomer is selected from one or more of the group consisting of methyl methacrylate, acrylic acid, methacrylic acid, 2-carboxyethyl acrylate, 2-carboxyethyl acrylate oligomers, acrylamide, methacrylamide, allylamine, (hydroxyethyl)methacrylate, hydroxypropyl methacrylate, 4-hydroxybutyl acrylate, glycidyl methacrylate, allyl glycidyl ether, 1,2-epoxy-5-hexene, maleic anhydride, optionally wherein the bulk monomer is selected from methacrylic acid and/or 2-hydroxyethyl methacrylate.

19. The beads according to any one of the preceding clauses, wherein the second functional monomer is selected from one or more of the group consisting of one or more of the group consisting of acrylic acid, methacrylic acid, 2-carboxyethyl acrylate, acrylamide, methacrylamide, allylamine, (hydroxyethyl)methacrylate, hydroxypropyl methacrylate, 4 -hydroxybutyl acrylate, glycidyl methacrylate, allyl glycidyl ether, 1,2-epoxy-5-hexene, maleic anhydride, 2-hydroxyethyl methacrylate, and 2-carboxyethyl acrylate oligomers.

20. The beads according to any one of the preceding clauses, wherein the second shell portion further comprises a crosslinking monomer in the first and/or second and/or third layer, optionally wherein the crosslinking monomer is selected from one or more of the group consisting of divinylbenzene, ethylene glycol dimethylacrylate, bisphenol A dimethacrylate, N,N'-methylenebis(acrylamide), bisphenol A epoxy acrylate, bisphenol diacrylate, tripropylene glycol diacrylate, propoxylated neopentyl diacrylate, propoxylated glycerol diacrylate, pentaerythritol propoxylate triacrylate, butandiol dimethacrylate, tricyclodecane dimethanol diacrylate, pentaerythritol triacrylate, ditrimethylolpropane tetraacrylate, dipentaerythritol penta/hexa-acrylate, tripropylene diacrylate, trimethylol propane ethoxylate triacrylate, trimethylol propane propoxylate triacrylate, di(trimethylolpropane) tetraacrylate, glycerol propoxylate triacrylate, poly(ethylene glycol) diacrylate, poly(propylene glycol) diacrylate, and tri(propylene glycol) diacrylate, for example the crosslinking monomer is selected from one or more of the group consisting of divinylbenzene, ethylene glycol dimethylacrylate, bisphenol A dimethacrylate, and N,N'-methylenebis(acrylamide).

21. The superparamagnetic beads according to any one of the preceding clauses, wherein the combined weight of the second and third layer of the second shell accounts for from 1-30 wt %, preferably 2-20 wt % of the entire weight of each bead.

22. A method of preparing monodisperse superparamagnetic beads, having a core-shell structure, the method comprising:

(a) providing monodisperse superparamagnetic precursor beads, which comprise a core portion formed from a polystyrene polymeric matrix material, where the polystyrene polymeric matrix material encapsulates a first batch of superparamagnetic $Fe_3O_4$ nanoparticles;

a first shell portion located directly on top of the core portion and formed from a crosslinked polymeric matrix material that is formed from a styrene monomer, a crosslinking monomer and a first functional monomer that has functional groups, where the copolymeric matrix material encapsulates a second batch of superparamagnetic $Fe_3O_4$ nanoparticles; and a second shell portion located directly on top of the first shell portion, which comprises superparamagnetic $Fe_3O_4$ nanoparticles and polymeric precursor anchor points, both which are bound to the functional groups on a surface of the first shell portion; and (b) forming a functional coating layer on the monodisperse superparamagnetic precursor beads by a one-pot free radical polymerization, which:

(i) in a first step uses a bulk monomer; and (ii) in a second step uses a second functional monomer that has functional groups to form the monodisperse superparamagnetic beads, wherein the functional coating layer is bound to the first shell portion by way of the polymeric precursor anchor points.

23. The process according to Clause 22, wherein the bulk monomer is selected from one or more of the group consisting of a polyether monomer, a polyester monomer, a polyacrylamide monomer, and polyacid monomer.

24. The process according to Clause 23, wherein the bulk monomer is selected from one or more of the group consisting of methyl methacrylate, acrylic acid, methacrylic acid, 2-carboxyethyl acrylate, 2-carboxyethyl acrylate oligomers, acrylamide, methacrylamide, allylamine, (hydroxyethyl)methacrylate, hydroxypropyl methacrylate, 4-hydroxybutyl acrylate, glycidyl methacrylate, allyl glycidyl ether, 1,2-epoxy-5-hexene, maleic anhydride, optionally wherein the bulk monomer is selected from methacrylic acid and/or 2-hydroxyethyl methacrylate.

25. The process according to any one of Clauses 22 to 24, wherein the first step uses a mixture comprising the bulk monomer and an initiator, optionally wherein the initiator is selected from one or more of the groups consisting of tertiary-amyl hydroperoxide, potassium persulfate, sodium persulfate, ammonia persulfate, 4,4'-azobis(4-cyanovaleric acid), 2,2'-azobis[2-methyl-N-(2-hydroxyethyl)propionamide, 2,2'-azobis[N-(2-carboxyethyl)-2-methylpropionamidine]hydrate, 2,2'-azobis(2-methylpropionamidine) dihydrochloride, 2,2''-azobis[2-(2-imidazolin-2-yl)propane], and 2,2'-azobis[2-(2-imidazolin-2-yl)propane]dihydrochloride.

26. The process according to Clause 25, wherein the mixture in the first step further comprises:

(a) a crosslinker, optionally wherein the crosslinker is selected from one or more of the group consisting of divinylbenzene, ethylene glycol dimethylacrylate, bisphenol A dimethacrylate, N,N'-methylenebis(acrylamide), bisphenol A epoxy acrylate, bisphenol diacrylate, tripropylene glycol diacrylate, propoxylated neopentyl diacrylate, propoxylated glycerol diacrylate, pentaerythritol propoxylate triacrylate, butandiol dimethacrylate, tricyclodecane dimethanol diacrylate, pentaerythritol triacrylate, ditrimethylolpropane tetraacrylate, dipentaerythritol penta/hexa-acrylate, tripropylene diacrylate, trimethylol propane ethoxylate triacrylate, trimethylol propane propoxylate triacrylate, di(trimethylolpropane) tetraacrylate, glycerol propoxylate triacrylate, poly(ethylene glycol) diacrylate, poly (propylene glycol) diacrylate, and tri(propylene glycol) diacrylate, for example the crosslinking monomer is selected from one or more of the group consisting of divinylbenzene, ethylene glycol dimethylacrylate, bisphenol A dimethacrylate, and N,N'-methylenebis(acrylamide); and/or (b) a solvent, optionally wherein the solvent is selected from one or more of the group consisting of 1,4-dioxane, tetrahydrofuran, diglyme, ethyl acetate, butyl acetate, acetone, methyl ethyl ketone, and water.

27. The process according to any one of Clauses 22 to 26, wherein the second functional monomer is selected from one or more of the group consisting of one or more of the group consisting of acrylic acid, methacrylic acid, 2-carboxyethyl acrylate, acrylamide, methacrylamide, allylamine, (hydroxyethyl)methacrylate, hydroxypropyl methacrylate, 4-hydroxybutyl acrylate, glycidyl methacrylate, allyl glycidyl ether, 1,2-epoxy-5-hexene, maleic anhydride, 2-hydroxyethyl methacrylate, and 2-carboxyethyl acrylate oligomers.

28. The process according to any one of Clauses 22 to 27, wherein:

(a) the polymerization of the first and/or second step is conducted at a temperature of from 30 to 80° C., such as from 50 to 70° C.; and/or (b) the total polymerization time for the first and second step is from 10 to 30 hours, such as from 16 to 24 hours.

29. The process according to any one of Clauses 22 to 28, wherein the monodisperse superparamagnetic precursor beads are formed by a process that comprises:

(i) providing naked monodisperse superparamagnetic beads, which comprise a core portion formed from a polystyrene polymeric matrix material, where the polystyrene polymeric matrix material encapsulates a first batch of superparamagnetic $Fe_3O_4$ nanoparticles;

a first shell portion located directly on top of the core portion and formed from a crosslinked polymeric matrix material that is formed from a styrene monomer, a crosslinking monomer and a first functional monomer that has functional groups, where the copolymeric matrix material encapsulates a second batch of superparamagnetic $Fe_3O_4$ nanoparticles; and a second shell portion located directly on top of the first shell portion, which comprises superparamagnetic $Fe_3O_4$ nanoparticles which is bound to the functional groups on a surface of the first shell portion; and (ii) forming the monodisperse superparamagnetic precursor beads by forming polymeric precursor anchor points on the first shell portion by reacting the naked monodisperse superparamagnetic beads with an anchoring material selected from one or more of the group consisting of methacryloyl chloride, 3-ethoxyacryloyl chloride, acryloyl chloride, 4-pentenoyl chloride, methacrylic anhydride, 4-pentenoic anhydride, crotonic anhydride, valeric anhydride, 10-undecenoyl chloride, glycidol methacrylate, glycidol, and allyl glycidyl ether.

30. The process according to Clause 29, wherein the naked monodisperse superparamagnetic beads are formed by a process that comprises:

(ai) providing monodisperse beads, which comprise:

a core portion formed from a polystyrene polymeric matrix material; and a first shell portion located directly on top of the core portion and formed from a crosslinked polymeric matrix material that is formed from a styrene monomer, a crosslinking monomer and a first functional monomer that has functional groups; and (aii) forming the naked monodisperse superparamagnetic beads by placing the monodisperse beads into a solution that comprises a Fe(III) salt and a Fe(II) salt and adding a base.

31. The process according to Clause 30, wherein:

(a) the Fe(III) salt is selected from $FeCl_3$ and/or $Fe_2(SO_4)_3$; and/or (b) the Fe(II) salt is selected from one or more of the group consisting of $FeCl_2$, $FeSO_4$, $Fe(OAC)_2$; and/or (c) the base is selected from one or more of the group consisting of ammonia hydroxide, NaOH, KOH, and amine; and/or (d) the solution further comprises $CoCl_2$ and/or $MnCl_2$.

32. The process according to Clause 30 or Clause 31, wherein the monodisperse beads are formed by a "one-pot three-stage" continuous process, which process comprises:

(a) in a first stage, generating a polystyrene core by dispersion polymerization of a styrene monomer with an initiator and a polymer stabilizer in a mixture of alcohol with water to form nucleated polystyrene cores;

(b) in a second stage, adding a crosslinking monomer to mixture comprising nucleated polystyrene cores; and (c) in a third stage adding a first functional monomer to the material obtained from the second stage to provide the monodisperse beads, optionally wherein the polystyrene beads are generated in situ, and the subsequent addition of crosslinker and functional monomers do not cause a second nucleation, thus leading to spherical monodisperse copolymer beads of (styrene/crosslinker/functional monomer) bearing functional groups on a surface.

33. The process according to clause 32, wherein:

(a) the initiator is selected from an azo initiator, optionally wherein the azo initiator is selected from one or more of the group consisting of 2,2'-azobis(2-methylpropionitrile) (AIBN), and 2,2'-azobis(2-methylbutyronitrile) (AMBN); and/or (b) the polymer stabilizer is selected from one or more of the group consisting of poly(vinylpyrrolidone) (PVP), polyethylenimine (PEI), polyacrylic acid (PAA), polyvinyl alcohol (PVA), hydroxypropyl methylcellulose (HPC), and chitosan; and/or (c) the styrene monomer is selected from one or more of the group consisting of styrene, and a styrene derivative, optionally wherein the styrene derivative is selected from one or more of the group consisting of 4-methylstyrene, 3-methylstyrene, and 4-tertbutylstyrene; and/or (d) the alcohol is selected from one or more of the group consisting of methanol, ethanol, isopropanol, or a mixture of them; and/or (e) the volume ratio of alcohol to water is from 1:1 to 40:1, such as from 2:1 to 20:1.

34. The process according to Clause 32 or Clause 33, wherein the crosslinking monomer is selected from one or more of the group consisting of divinylbenzene, ethylene glycol dimethylacrylate, bisphenol A dimethacrylate, butanediol dimethacrylate, tricyclodecane dimethanol diacrylate, pentaerythritol triacrylate, tripropylene glycol diacrylate, propoxylated neopentyl diacrylate, pentaerythritol triacrylate, ditrimethylolpropane tetraacrylate, dipentaerythritol pentaacrylate, dipentaerythritol penta/hexa-acrylate, tripropylene diacrylate, trimethylol propane ethoxylate triacrylate, trimethylol propane propoxylate triacrylate, di(trimethylolpropane) tetraacrylate, glycerol propoxylate triacrylate, pentaerythritol propoxylate triacrylate, poly(ethylene glycol) diacrylate, poly(propylene glycol) diacrylate, and tri(propylene glycol) diacrylate, optionally wherein the crosslinking monomer is selected from one or more of the group consisting of divinylbenzene, ethylene glycol dimethylacrylate, bisphenol A dimethacrylate, and N,N'-methylenebis(acrylamide).

35. The process according to any one of Clauses 32 to 34, wherein the functional groups on the first functional monomer are independently selected from one or more of amino, carboxyl, epoxy, and hydroxyl, optionally wherein the functional groups on the functional monomer in the first shell portion and the second layer of the second shell portion are independently selected from a combination of hydroxyl and carboxyl groups or a combination of amino and carboxyl groups.

36. The process according to clause 35, wherein the first functional monomer is selected from one or more of the group consisting of acrylic acid, methacrylic acid, 2-carboxyethyl acrylate, acrylamide, methacrylamide, allylamine, (hydroxyethyl)methacrylate, hydroxypropyl methacrylate, 4-hydroxybutyl acrylate, glycidyl methacrylate, allyl glycidyl ether, 1,2-epoxy-5-hexene, maleic anhydride, 2-hydroxyethyl methacrylate, and 2-carboxyethyl acrylate oligomers.

37. The process according to any one of Clauses 32 to 36, wherein, the weight ratio of the styrene monomer to crosslinker is from 20:1 to 1:2, such as from 10:1 to 1:1.

38. The process according to any one of Clauses 32 to 37, wherein the weight ratio of the styrene monomer to first functional monomer is between 20:1 to 1:2, preferably between 10:1 to 1:1.

39. The process according to any one of Clauses 32 to 37, wherein the as-synthesized monodisperse beads are washed with one or more solvents before use in a subsequent process step, optionally wherein the solvent is selected from one or more of the group consisting of water, methanol, ethanol, isopropanol, and THF.

40. The process according to any one of Clauses 22 to 39, wherein the resulting monodisperse superparamagnetic beads have:

(a) a coefficient of variation based on their diameter of less than 15%, such as less than 10%, such as less than 5%, such as less than or equal to 2%; and/or (b) an average diameter of from 0.2 to 5.0 microns, such as from 0.5 to 4.0 microns.

41. The superparamagnetic beads according to any one of the preceding clauses, wherein these beads are applied in IVD assays.

DESCRIPTION

Figure 1:
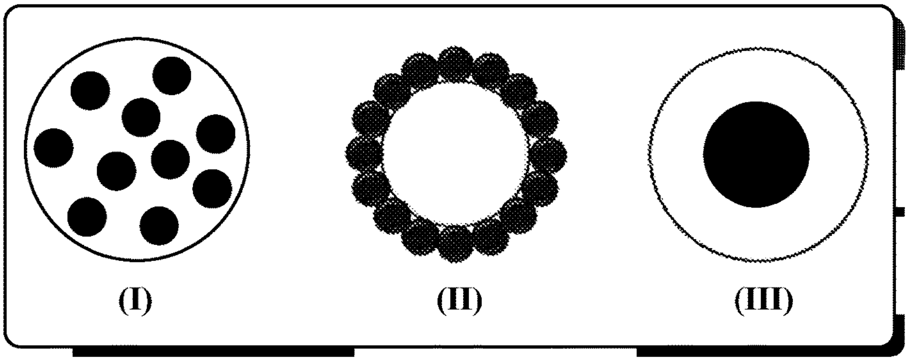
FIG. 1 schematically depicts three types of magnetic polymer beads. Type (I): magnetic NPs distributed in the polymer bead; Type (II): a magnetic shell and a polymer core. Type (III): a polymer shell and a magnetic core.

It has been surprisingly found that the problems above can be solve, in whole or in part, by the introduction of a new type of monodisperse superparamagnetic bead. These monodisperse superparamagnetic beads have superparamagnetic NPs distributed throughout the core and shell(s) of the beads. It has been surprisingly found that these beads can be loaded with $Fe_3O_4$ nanoparticles over a wide range of weight percentages (e.g. from 30 wt % to over 50 wt % of the total weight of the bead), without suffering from the problems described above. It is believed that these beads will improve the efficiency of downstream separation process and also the final application in IVD processes.

Thus, disclosed herein are monodisperse superparamagnetic beads, having a core-shell structure, said bead comprising:

a core portion formed from a polystyrene polymeric matrix material, where the polystyrene polymeric matrix material encapsulates a first batch of superparamagnetic $Fe_3O_4$ nanoparticles;

a first shell portion located directly on top of the core portion and formed from a crosslinked polymeric matrix material that is formed from a styrene monomer, a crosslinking monomer and a first functional monomer that has functional groups, where the copolymeric matrix material encapsulates a second batch of superparamagnetic $Fe_3O_4$ nanoparticles; and a second shell portion located directly on top of the first shell portion, which is formed as a first layer, a second layer and a third layer, the first layer comprises superparamagnetic $Fe_3O_4$ nanoparticles and a first layer polymeric matrix material that comprises a conjugating monomer and a bulk monomer;

a second layer extending beyond the first layer, which is formed from a second layer polymeric material that comprises a bulk monomer; and a third layer on top of the second layer, which is formed from a third layer polymeric material that comprises a bulk monomer and a second functional monomer that has functional groups, wherein:

the superparamagnetic $Fe_3O_4$ nanoparticles in the first layer are directly bound to the functional groups present on an outer surface of the first shell portion;

the first layer polymeric matrix material surrounds the superparamagnetic $Fe_3O_4$ nanoparticles in the first layer; and the second layer polymeric matrix material extends from the first layer polymeric matrix material and forms an outer surface of each monodisperse superparamagnetic bead.

The word "comprising" refers herein may be interpreted as requiring the features mentioned, but not limiting the presence of other features. Alternatively, the word "comprising" may also relate to the situation where only the components/features listed are intended to be present (e.g. the word "comprising" may be replaced by the phrases "consists of" or "consists essentially of"). It is explicitly contemplated that both the broader and narrower interpretations can be applied to all aspects and embodiments of the present invention. In other words, the word "comprising" and synonyms thereof may be replaced by the phrase "consisting of" or the phrase "consists essentially of" or synonyms thereof and vice versa.

The term "particles" when used herein is intended to be synonymous with the terms "beads" and "microspheres". The term "polymer particles" when used herein is intended to be synonymous with the terms "polymer beads" and "polymer microspheres". The term "superparamagnetic polymer particles" when used herein is intended to be synonymous with the terms "superparamagnetic polymer beads" and "superparamagnetic polymer microspheres".

The term "monodisperse" when used herein refers to particles having a low coefficient of variation (CV) of a specific parameter (e.g. particle diameter), for example a CV of less than 20%, such as less than 15%, such as less than 10%, such as less than 5%. More particularly, the particles may have a CV of less than or equal to 2%, such as less than or equal to 1%. The term "monodisperse" also encompasses the term "highly monodisperse", which, when used herein, may refer to a CV of less than 5%, such as less than or equal to 2%, such as less than or equal to 1%.

When used herein, the term "coefficient of variation" refers to its statistical meaning. That is:

$$CV\ (\%) = \frac{\text{standard deviation}}{\text{mean}} \times 100$$

The terms "standard deviation" and "mean" take their ordinary statistical meanings.

Mention in this specification of "average" diameters refers to the average diameter obtained from scanning electron microscopy (SEM).

The magnetic NPs refers herein may comprise at least one kind of paramagnetic NPs, superparamagnetic NPs, ferromagnetic NPs or ferrimagnetic NPs. The definitions are listed below.

"Magnetic" when used herein means a property of responding to a magnetic field in a material. "Paramagnetic" when used herein means that the magnetic property displayed by a material is switched off after the external magnetic field is removed. "Superparamagnetic" when used herein means that the magnetic property of a material is switched-off instantly upon removal of the external magnetic field.

"Ferromagnetic" when used herein means that all the magnetic atoms within each domain contribute a positive value to the overall net magnetization of the material, which retains magnetic properties after an external magnetic field is removed. Said material becomes paramagnetic material above its Curie temperature.

"Ferrimagnetic" when used herein means that some of magnetic atoms within each domain are opposed, but the material overall exhibits net magnetization. Said material retains its magnetic property after an external magnetic field is removed. Said material becomes a paramagnetic material above its Curie temperature.

Figure 12:
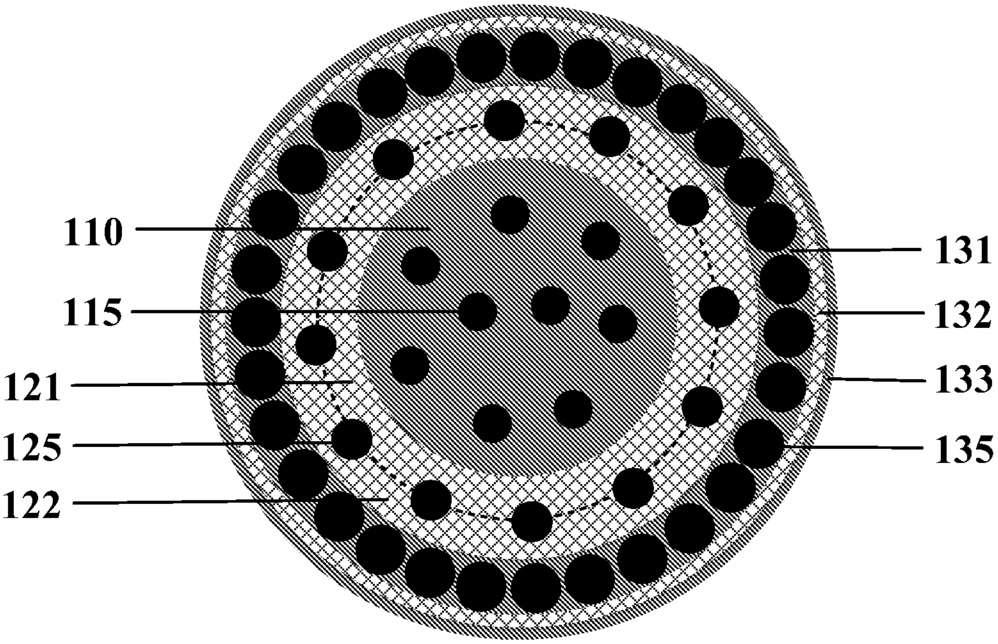
FIG. 12 schematically depicts the fully-formed monodisperse superparamagnetic bead in detail.

FIG. 2D illustrates in cartoon form a fully-formed monodisperse superparamagnetic bead according to the current invention. FIG. 12 illustrates the fully-formed monodisperse superparamagnetic bead in more detail. FIG. 12 illustrates a cross-section of a monodisperse superparamagnetic bead 100 according to the current invention. The bead has a core 110, a first shell 120 and a second shell 130. The core 110 is formed of a polystyrene polymeric matrix material 111, where the core polymeric matrix material contains pores 112 that encapsulate a portion of superparamagnetic $Fe_3O_4$ nanoparticles 115.

The first shell portion 120 may be in the form of a single layer (not illustrated) or two layers (121, 122). When in the form of a single layer, the first shell portion has a crosslinked polymeric matrix material that is formed from a styrene monomer, a crosslinking monomer and a first functional monomer that has functional groups. When in the form of two layers, the first layer may be a crosslinked polymeric matrix material 123 formed from a copolymer of a styrene monomer and a crosslinking monomer, with the second layer 124 being formed from a copolymer a styrene monomer, a crosslinking monomer and a functional monomer. Again, the polymeric matrix material(s) in the first shell portion may encapsulate $Fe_3O_4$ nanoparticles 125.

The second shell portion 130 is formed from three layers (131, 132, 133). The first layer contains $Fe_3O_4$ nanoparticles 134, which are bound to functional groups provided on the surface of the first shell portion 120. In addition, the first layer also contains a first layer of polymeric matrix material 135 that comprises a conjugating monomer and a bulk monomer. Thus a first layer of polymeric matrix material extends from the surface of the first shell portion to about the top of the $Fe_3O_4$ nanoparticles 134. The second layer 132 extends beyond the first layer (and hence beyond the top of the $Fe_3O_4$ nanoparticles 134) and this layer is formed from a second layer polymeric material that comprises a bulk monomer. A third layer 133 is formed on top of the second layer, which is formed from a third layer polymeric material that comprises a bulk monomer and a second functional monomer that has functional groups.

When used herein "encapsulate" may refer to the full encapsulation of a material within another material or it may also refer to the partial encapsulation of a material within another material. The term may also refer to the situation where a material is trapped within a pore of another material.

It is noted that the second and third layers of polymeric matrix materials in the second shell portion function to prevent the superparamagnetic magnetic ($Fe_3O_4$) nanoparticles from leaching out when the beads are placed into a solvent. This is possible because, as described below, the polymeric portion of the second shell is formed following the loading of the surface of the first shell (and core) of the nascent beads with $Fe_3O_4$ nanoparticles. This allows the polymeric shell that is formed to act as a barrier to protect the $Fe_3O_4$ nanoparticles from leakage.

Any suitable functional groups may be present on the functional monomer used in the first shell portion and in the third layer of the second shell portion. As will be appreciated, the desired functions of the functional groups on the first shell portion and the third layer of the second shell portion are different. The functional groups on the (surface of the) first shell portion are intended to bind to the $Fe_3O_4$ nanoparticles, such that the $Fe_3O_4$ nanoparticles are bound to the surface of the first shell portion. This binding may be by any suitable chemical interaction, such as by coordination, covalent bonding, electrostatic forces or hydrogen bonding. The functional groups in the third layer of the second shell portion are intended to enable the easy functionalisation of the fully-formed beads for any suitable intended application (e.g. covalently binding a ligand or antibody to the surface of the fully-formed beads). Nevertheless, the functional groups on the functional monomer in the first shell portion and the third layer of the second shell portion may be independently selected from one or more of amino, carboxyl, epoxy, and hydroxyl. For example, the functional groups on the functional monomer in the first shell portion and the second layer of the second shell portion may independently be selected from a combination of hydroxyl and carboxyl groups or a combination of amino and carboxyl groups.

The beads of the current invention are monodisperse as defined hereinbefore. More particularly, the beads disclosed herein may have a coefficient of variation based on their diameter of less than 15%, such as less than 10%, such as less than 5%. Yet more particularly, the beads disclosed herein may be highly monodisperse as defined hereinbefore. For example, the beads may have a coefficient of variation based on their diameter of less than or equal to 2%.

The beads disclosed herein may have any suitable average diameter that makes them useful in the intended applications (e.g. IVD). Examples of a suitable average diameter is from 0.2 to 5.0 μm, such as from 0.5 to 4.0 μm.

As noted above, the core is formed from a polystyrene matrix material. This may be formed from a homopolymer of any suitable styrene monomer or a copolymer of two or more (e.g. 2, 3, 4, 5 or 6) styrene monomers. As will be appreciated, when used herein, the term "a styrene monomer" is to be interpreted as covering the class of styrene monomers in general—that is styrene per se and its monomeric derivatives. Examples of suitable styrene monomers that may be used to form the polystyrene polymeric matrix material include, but are not limited to, styrene, a styrene derivative, and copolymers thereof. In particular embodiments that may be mentioned herein, the styrene derivative may be selected from one or more of the group consisting of 4-methylstyrene, 3-methylstyrene, and 4-tertbutylstyrene. The core polystyrene matrix material may be a material that is not crosslinked.

As noted above, it has been surprisingly found that the beads disclosed herein may have a wide range of loading values for the superparamagnetic $Fe_3O_4$ nanoparticles, without suffering from the problems encountered by conventional designs. For example, all of the superparamagnetic $Fe_3O_4$ nanoparticles in a bead may account for from 10 to 80 wt %, such as from 20 to 70 wt %, such as from 30 to 50 wt % of the entire weight of each bead. In particular embodiments that may be mentioned herein, all of the superparamagnetic $Fe_3O_4$ nanoparticles in a bead may account for from 30 to 50 wt % of the entire weight of each bead. As will be appreciated, the amount of the superparamagnetic $Fe_3O_4$ nanoparticles distributed in each portion of the beads varies. For example, one or more of the following loading distributions may apply:

(a) the first batch of superparamagnetic $Fe_3O_4$ nanoparticles may represent from 0.1 to 5 wt % of the entire weight of each bead;

(b) the second batch of superparamagnetic $Fe_3O_4$ nanoparticles may represent from 0.5 to 10 wt % of the entire weight of each bead; and (c) the superparamagnetic $Fe_3O_4$ nanoparticles in the first layer of the second shell portion may represent from 9.4 to 79.4 wt %, such as from 19.4 to 69.4 wt %, such as from 29.4 to 49.4 wt % of the entire weight of each bead.

As noted hereinbefore, a crosslinking monomer is used to form the crosslinked polymeric matrix material in the first shell portion. It is believed that the inclusion of crosslinks within the beads provides them with stiffness and/or mechanical strength, as well as resistance to swelling that may otherwise be caused by solvents. Any suitable crosslinking monomer may be used to form the crosslinks in the first shell portion of the beads. A suitable crosslinking monomer may be selected from one or more of the group consisting of divinylbenzene, ethylene glycol dimethylacrylate, bisphenol A dimethacrylate, butanediol dimethacrylate, tricyclodecane dimethanol diacrylate, pentaerythritol triacrylate, tripropylene glycol diacrylate, propoxylated neopentyl diacrylate, pentaerythritol triacrylate, ditrimethylolpropane tetraacrylate, dipentaerythritol pentaacrylate, dipentaerythritol penta/hexa-acrylate, tripropylene diacrylate, trimethylol propane ethoxylate triacrylate, trimethylol propane propoxylate triacrylate, di(trimethylolpropane) tetraacrylate, glycerol propoxylate triacrylate, pentaerythritol propoxylate triacrylate, poly(ethylene glycol) diacrylate, poly(propylene glycol) diacrylate, and tri(propylene glycol) diacrylate. In particular embodiments of the invention that may be mentioned herein, the crosslinking monomer may be selected from one or more of the group consisting of divinylbenzene, ethylene glycol dimethylacrylate, bisphenol A dimethacrylate, and N,N-methylenebis(acrylamide).

In keeping with the functional groups discussed above, the first functional monomer in the crosslinked polymeric matrix material may be selected from one or more of the group consisting of acrylic acid, methacrylic acid, 2-carboxyethyl acrylate, acrylamide, methacrylamide, allylamine, (hydroxyethyl)methacrylate, hydroxypropyl methacrylate, 4-hydroxybutyl acrylate, glycidyl methacrylate, allyl glycidyl ether, 1,2-epoxy-5-hexene, maleic anhydride, 2-hydroxyethyl methacrylate, and 2-carboxyethyl acrylate oligomers. As will be appreciated, the specific combinations of functional groups discussed above may be obtained by selection from these monomers.

The crosslinked polymeric matrix material in the first shell portion is also formed by the use of a styrene monomer. As before, the styrene monomer may be selected from one or more of the group consisting of styrene, and a styrene derivative. As before, the styrene derivative may be selected from one or more of the group consisting of 4-methylstyrene, 3-methylstyrene, and 4-tertbutylstyrene.

As mentioned above, the first shell portion may be formed from two layers of material, instead on a single layer of material. That is, there may be a first layer of a first polymeric matrix composition and a second layer of a second polymeric matrix composition. In embodiments with two layers:

the first layer may be formed from a copolymer of a styrene monomer and a crosslinking monomer; and the second layer may be formed from a copolymer a styrene monomer, a crosslinking monomer and a functional monomer.

The styrene monomer, crosslinking monomer and functional monomer are as described above. It will be appreciated that the actual demarcation between the two layers may not be entirely clear. This is because the method of manufacture may involve the addition of the copolymer of a styrene monomer and a crosslinking monomer to form the first layer, followed at a later stage by the addition of the functional monomer to form the second layer. As such, a portion of the first layer may also contain the functional monomer. For the avoidance of doubt, the second layer is intended to form the outer surface of the first shell portion and is therefore desired to present functional groups that are capable of bonding to superparamagnetic $Fe_3O_4$ nanoparticles and/or to conjugating monomers (the latter to enable the formation of the polymeric portion of the second shell portion). Further details of the manufacture of the first shell portion will be provided below and in the experimental section.

As noted above, the beads described herein contain superparamagnetic $Fe_3O_4$ nanoparticles. These superparamagnetic $Fe_3O_4$ nanoparticles may have any suitable diameter that allows them to fall within the conventional definition of "nanoparticles". However, in particular embodiments of the invention that may be mentioned herein, the superparamagnetic $Fe_3O_4$ nanoparticles may have an average diameter of from 5 to 15 nm.

In embodiments of the invention that are mentioned herein, the weight to weight ratio of styrene groups to crosslinking groups in the core portion and first shell portion may be from from 20:1 to 1:2, such as from 10:1 to 1:1. In additional or alternative embodiments that may be mentioned herein, the weight to weight ratio of styrene groups to functional groups in the core portion and first shell portion may be from 20:1 to 1:2, such as from 10:1 to 1:1. Reference to the core portion and first shell portion is intended to mean that the combined weights in these portions should be considered when determining the overall loading of the components mentioned. For example, while the core portion does not contain crosslinking groups or functional groups, the weight of its styrene groups should be taken into account when determining the relative weight ratios of these components to the total weight of styrene groups in the core portion and first shell portion.

In certain embodiments of the invention that may be mentioned herein, the $Fe_3O_4$ nanoparticles also contain a portion of $Co_3O_4$ and/or $Mn_3O_4$ nanoparticles. Any suitable amount of $Co_3O_4$ and/or $Mn_3O_4$ nanoparticles may be present in addition to the $Fe_3O_4$ nanoparticles. For the avoidance of doubt, when the weight percentage of the $Fe_3O_4$ nanoparticles compared to the weight of the beads is provided herein, the weight of the $Fe_3O_4$ nanoparticles includes the weight of any $Co_3O_4$ and/or $Mn_3O_4$ nanoparticles that are present.

The second shell portion is formed from three separate layers of material, as discussed above. The first layer is formed in part by the $Fe_3O_4$ nanoparticles, which are directly bound to the functional groups present on an outer surface of the first shell portion. This first layer also contains a first layer polymeric matrix material that comprises a conjugating monomer and a bulk monomer. The conjugating monomer is a compound that is used as an anchoring point on the surface of the first shell portion. As such, the conjugating monomer itself contains a functional group that can react with the functional groups on the surface of the first shell portion, as well as a functional group that can be used in a polymerisation reaction. Any suitable conjugating monomer may be used herein. Examples of suitable conjugating monomers include, but are not limited to, methacryloyl chloride, 3-ethoxy-acryloyl chloride, acryloyl chloride, 4-pentenoyl chloride, methacrylic anhydride, 4-pentenoic anhydride, crotonic anhydride, valeric anhydride, 10-undecenoyl chloride, glycidol methacrylate, glycidol, allyl glycidyl ether, and combinations thereof.

The bulk monomer that forms part of the first and second layers of the second shell portion may be selected from one or more of a polyether monomer, a polyester monomer, a polyacrylamide monomer, and a polyacid monomer. Examples of suitable bulk monomers include, but are not limited to, methyl methacrylate, acrylic acid, methacrylic acid, 2-carboxyethyl acrylate, 2-carboxyethyl acrylate oligomers, acrylamide, methacrylamide, allylamine, (hydroxyethyl)methacrylate, hydroxypropyl methacrylate, 4-hydroxybutyl acrylate, glycidyl methacrylate, allyl glycidyl ether, 1,2-epoxy-5-hexene, maleic anhydride, and combinations thereof. In particular embodiments that may be mentioned herein the bulk monomer may be selected from methacrylic acid and/or 2-hydroxyethyl methacrylate.

As noted hereinbefore, the third layer of the second shell portion may be formed from a second functional monomer. The functional groups on this second functional monomer may be as described hereinbefore. Examples of suitable functional monomers include, but are not limited to, one or more of acrylic acid, methacrylic acid, 2-carboxyethyl acrylate, acrylamide, methacrylamide, allylamine, (hydroxyethyl)methacrylate, hydroxypropyl methacrylate, 4-hydroxybutyl acrylate, glycidyl methacrylate, allyl glycidyl ether, 1,2-epoxy-5-hexene, maleic anhydride, 2-hydroxyethyl methacrylate, and 2-carboxyethyl acrylate oligomers.

The polymeric materials used in the second shell portion may also be crosslinked. For example, the first layer may be crosslinked, the second layer may be crosslinked, the third layer may be crosslinked or any combination thereof. In embodiments that may be mentioned herein, the first layer and the second layer may be crosslinked, with the third layer having no or less crosslinking relative to the other layers.

The crosslinking monomer used to form crosslinks in the second shell portion may be selected from one or more of the group consisting of divinylbenzene, ethylene glycol dimethylacrylate, bisphenol A dimethacrylate, N,N'-methylenebis(acrylamide), bisphenol A epoxy acrylate, bisphenol diacrylate, tripropylene glycol diacrylate, propoxylated neopentyl diacrylate, propoxylated glycerol diacrylate, pentaerythritol propoxylate triacrylate, butandiol dimethacrylate, tricyclodecane dimethanol diacrylate, pentaerythritol triacrylate, ditrimethylolpropane tetraacrylate, dipentaerythritol penta/hexa-acrylate, tripropylene diacrylate, trimethylol propane ethoxylate triacrylate, trimethylol propane propoxylate triacrylate, di(trimethylolpropane) tetraacrylate, glycerol propoxylate triacrylate, poly(ethylene glycol) diacrylate, poly(propylene glycol) diacrylate, and tri(propylene glycol) diacrylate, for example the crosslinking monomer is selected from one or more of the group consisting of divinylbenzene, ethylene glycol dimethylacrylate, bisphenol A dimethacrylate, and N,N'-methylenebis(acrylamide).

In embodiments that may be disclosed herein, the combined weight of the second and third layer of the second shell may account for from 1-30 wt %, preferably 2-20 wt % of the entire weight of each bead.

Advantages associated with beads disclosed herein include, but are not necessarily limited to, the following.

- Among the three monomers, (a) styrene provides nucleation template, leading to spherical monodisperse beads; (b) crosslinker, such as DVB provides crosslinking, rending the beads stiffness to tolerant organic solvents; (c) The functional monomer facilitates the upload of superparamagnetic nanoparticles (NPs).
- The obtained copolymer beads of three monomers (styrene, crosslinker, functional monomer) are spherical and highly monodisperse, the beads diameter can be tuned by regulating the polymerization factors, such as the initiator concentration, PVP concentration, loading amount of monomers.
- Various monomers carrying functional groups can be used in the beads—both on the first shell surface and the second shell surface. This allows for a fine-tuning of the surface properties of the beads, allowing them to be more readily used in specific applications.
- The density of functional groups on beads surface can be fine-tuned by regulating the loading amount of the functional monomers (i.e. monomers carrying functional groups).
- High loading of superparamagnetic $Fe_3O_4$ NPs (30-50 wt %) on the beads can be achieved by on-site generation of NPs.
- The size of $Fe_3O_4$ NPs formed on the surface are well-controlled due to the well-controlled functional group grafting on the PS core.

As will be appreciated, the structure and many advantages associated with the beads described herein arise due to the method of manufacture of the beads.

In this invention, the monodisperse superparamagnetic beads are obtained through 4 steps:

Step-1: Synthesis of highly monodisperse copolymer beads of three monomers (styrene, crosslinker, functional monomer) via a "one-pot three-stage" polymerization procedure.

Step-2: Washing and surface modification of the as-synthesized copolymer beads with organic solvents.

Step-3: On-site generation and upload superparamagnetic $Fe_3O_4$ NPs on copolymer beads.

Step-4: Fabrication of functional coating on superparamagnetic beads.

Figure 2:
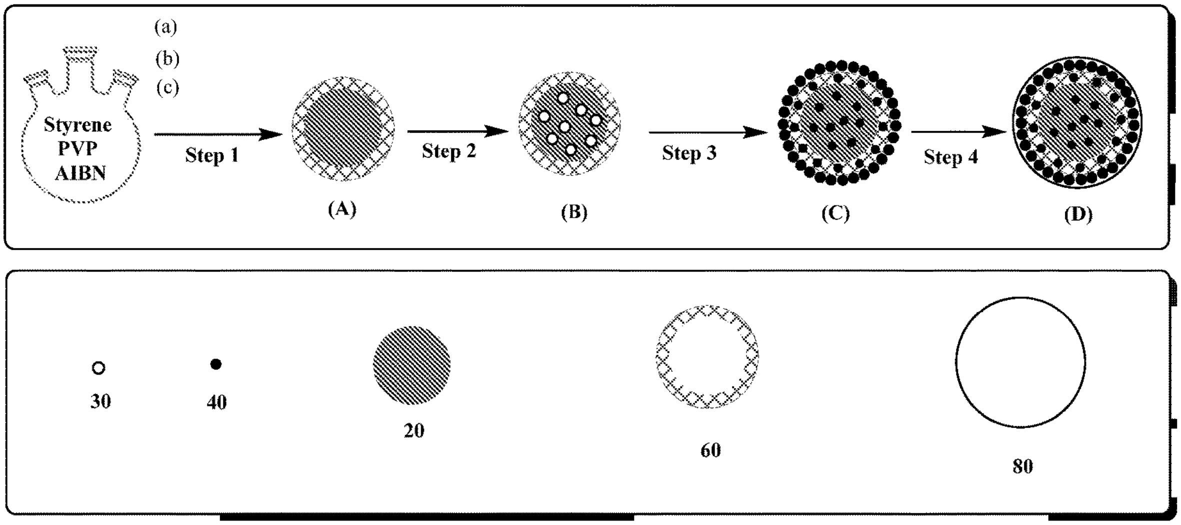
FIG. 2 schematically depicts a process for making spherical monodisperse superparamagnetic beads.

It is believed by the inventors that the procedure outlined above is a new process for the production of monodisperse superparamagnetic beads, which is fundamentally different from conventional synthetic methods used to make such beads. This process is outlined in FIG. 2, where FIG. 2A corresponds to the product obtained after step 1, FIG. 2B corresponds to the product obtained after step 2, FIG. 2C corresponds to the product obtained after step 3, and FIG. 2D corresponds to the final product obtained after step 4. In FIG. 2, 30 represents pores, 40 represents $Fe_3O_4$ NPs, 60 represents the polymeric part of the first shell portion and 80 represents the second shell portion.

More detail for each of the steps is provided below.

Step 1: Synthesis of highly monodisperse copolymer beads using three monomers (styrene, a crosslinker, and functional monomers) via a "one-pot three-stage" procedure, which provides the core and the first shell polymeric material (but does not contain the $Fe_3O_4$ nanoparticles). The stages of this process step are summarised below, (a) The first stage is a dispersion polymerization of styrene in a solvent (e.g. ethanol containing 1-20 v % water). Nucleation is completed in this step and most of styrene (such as 60-80 wt %) is consumed, thus the number of beads is fixed in this stage. The solvent may be a mixture of alcohol containing 1-20 v % water. The total polymerization time in the first stage may be from 2-12 hours, such as from 4-10 hours.

(b) The second stage is cross-linking by addition of crosslinker, the cross-linking copolymerization of crosslinker with the rest of the styrene monomer forms a core-shell structure (see A in FIG. 2). The weight percentage of cross-linker to styrene may be from 1 to 40 wt %, such as from 5 to 30%. In this stage, the polymerization time may be from 1 to 8 hours, such as from 2-6 hours.

(c) In the third stage, a functional monomer is added to copolymerize with the remaining amount of crosslinker and styrene, thus introducing hydrophilic functional groups to the surface of the beads. In addition, more than one functional monomer (such as two or three functional monomers) can be added together at this stage, which introduces multi-functional groups in one step. The weight percentage of functional monomer to styrene may be from 1 to 30 wt %, such as from 5-20%. In this stage, the polymerization time may be from 8-24 hours, such as from 10 to 20 hours.

This "one-pot three-stage" polymerization step may be conducted at any suitable temperature, such as from 40 to 80° C., such as from 50 to 70° C.

Step 2: The as-synthesized copolymer beads from step 1 are thoroughly washed with organic solvents. The aim of washing is to remove the unreacted styrene, crosslinker and functional monomers, as well as stabiliser (when used), such as PVP from the beads. In addition, washing with polar solvents can also remove some linear polystyrene from the polymer matrix, which may loosen the beads and may generate some pores to enable the loading of superparamagnetic $Fe_3O_4$ NPs in the core and within the first shell of the beads. The washed beads can be redispersed into a solvent (e.g. water) for storage (see B in FIG. 2).

In this washing step, the beads can be washed with one or more of water, methanol, ethanol, isopropanol, THF, and a mixture of these solvents. The beads can be soaked into the solvent for several hours to remove some linear polystyrene to loosen the beads or generate some pores inside the beads. During the washing or soaking process, the functional groups on the beads surface can be further modified to facilitate the uploading of superparamagnetic $Fe_3O_4$ NPs. When epoxy groups are introduced to the surface of the beads, the epoxy groups may undergo a ring-opening hydrolysis, or a ring-opening aminolysis, or ring-opening polymerization during the soaking process, to further modify the surface of the beads. This will depend on the nature of the solvents used, or any reagents added to said solvents for this washing step.

Step 3: The washed beads are dispersed into a solution (e.g. an aqueous solution, such as a mixture of water and polar solvent (e.g. THF)) containing $Fe^{3+}$ and $Fe^{2+}$ ions in a suitable molar ratio (e.g. a 2:1 molar ratio of $Fe^{3+}$:$Fe^{2+}$ ions). The temperature of the solution may then be increased (e.g. to 70° C.) with stirring for several hours to let the two ions to interact with the functional groups on the surface of the bead. Some $Fe^{3+}$ and $Fe^{2+}$ ions will penetrate into the beads' polymer matrix while some will be adsorbed onto the surface of the beads (through interaction with the functional groups on the surface of the beads as formed—i.e. the first shell surface). Aqueous ammonia is then added to transform the $Fe^{3+}$ and $Fe^{2+}$ ions into $Fe_3O_4$ NPs in situ. Before the addition of aqueous ammonia, ligands to stabilize $Fe_3O_4$ NPs, such as polyacrylic acid or tartaric acid or citric acid may be added to the solution to assist the formation of superparamagnetic $Fe_3O_4$ NPs. The obtained superparamagnetic polymer beads (see C in FIG. 2) are separated by centrifuge and washed with water and methanol to remove any loose $Fe_3O_4$ NPs.

The additive ligand to help stabilise the formation of the $Fe_3O_4$ NPs can be polyacrylic acid, tartaric acid, citric acid or a mixture of them.

Step 4: A coating layer is fabricated on the superparamagnetic polymer beads by grafting a polymeric network around the $Fe_3O_4$ NPs. To achieve polymer grafting, one or more compounds that can react with the functional groups on the first shell surface is used. This material is bifunctional, as it has a first functional group that can react with the functional groups on the surface of the first shell and a second functional group that can participate in polymerisation reactions. Once this compound has been anchored to the surface of the bead, it is then subjected to free radical polymerisation conditions using a bulk monomer and, optionally, a crosslinking agent. Then, subsequently, one or more monomers having desirable functional groups for down-stream processing or desired final functionality is added to the polymerisation mixture to provide the final portion of the second shell.

In step 4 of the above process, the superparamagnetic $Fe_3O_4$ NPs are bound together by functional polymeric network grafted from the surface of the step 2. To achieve polymer grafting, a monomer is modified on the surface through reaction with the functional groups left on the beads surface in step 2, for example, the excess of hydroxyl group or amine group. An anhydrous solvent is used in this step, which may be chosen from one or more of 1,4-dioxane, tetrahydrofuran, diglyme, ethyl acetate, butyl acetate, acetone, methyl ethyl ketone. Specific solvents that may be used in this step hereinbelow may be tetrahydrofuran and diglyme. The reaction time may be from 12 to 36 hours, with inert gas purging. The resulting beads will be washed with organic solvent to remove excess monomer.

When needed, an initiator may be used in the processes described above. The initiator may be chosen from azo initiators, such as AIBN, AMBN. The initiator can also be chosen from peroxide initiators and persulfate salts, including tertiary-amyl hydroperoxide, potassium persulfate, sodium persulfate and ammonia persulfate.

The weight percentage of crosslinker to bulk monomer may be from 5 to 70 wt %, preferably from 10 to 50%. In step 4, the polymerization time may be from 10 to 30 hours, such as from 16 to 24 hours. In step 4, the free-radical polymerization can be carried out at a temperature of from 40 to 80° C., such as from 50 to 70° C.

Thus, there is also disclosed a method of preparing monodisperse superparamagnetic beads, having a core-shell structure, the method comprising:

(a) providing monodisperse superparamagnetic precursor beads, which comprise a core portion formed from a polystyrene polymeric matrix material, where the polystyrene polymeric matrix material encapsulates a first batch of superparamagnetic $Fe_3O_4$ nanoparticles;

a first shell portion located directly on top of the core portion and formed from a crosslinked polymeric matrix material that is formed from a styrene monomer, a crosslinking monomer and a first functional monomer that has functional groups, where the copolymeric matrix material encapsulates a second batch of superparamagnetic $Fe_3O_4$ nanoparticles; and a second shell portion located directly on top of the first shell portion, which comprises superparamagnetic $Fe_3O_4$ nanoparticles and polymeric precursor anchor points, both which are bound to the functional groups on a surface of the first shell portion; and (b) forming a functional coating layer on the monodisperse superparamagnetic precursor beads by a one-pot free radical polymerization, which:

(i) in a first step uses a bulk monomer; and (ii) in a second step uses a second functional monomer that has functional groups to form the monodisperse superparamagnetic beads, wherein the functional coating layer is bound to the first shell portion by way of the polymeric precursor anchor points.

The bulk monomer may be selected from one or more of the group consisting of a polyether monomer, a polyester monomer, a polyacrylamide monomer, and polyacid monomer. For example, the bulk monomer may be selected from one or more of the group consisting of methyl methacrylate, acrylic acid, methacrylic acid, 2-carboxyethyl acrylate, 2-carboxyethyl acrylate oligomers, acrylamide, methacrylamide, allylamine, (hydroxyethyl)methacrylate, hydroxypropyl methacrylate, 4-hydroxybutyl acrylate, glycidyl methacrylate, allyl glycidyl ether, 1,2-epoxy-5-hexene, maleic anhydride, optionally wherein the bulk monomer is selected from methacrylic acid and/or 2-hydroxyethyl methacrylate.

In the method discussed directly above, the first step may use a mixture comprising the bulk monomer and an initiator. In this case, the initiator may be selected from one or more of the groups consisting of tertiary-amyl hydroperoxide, potassium persulfate, sodium persulfate, ammonia persulfate, 4,4'-azobis(4-cyanovaleric acid), 2,2'-azobis[2-methyl-N-(2-hydroxyethyl)propionamide, 2,2'-azobis[N-(2-carboxyethyl)-2-methylpropionamidine]hydrate, 2,2'-azobis(2-methylpropionamidine) dihydrochloride, 2,2"-azobis[2-(2-imidazolin-2-yl)propane], and 2,2'-azobis[2-(2-imidazolin-2-yl)propane]dihydrochloride. This mixture may also further comprise:

(a) a crosslinker. For example, the crosslinker may be selected from one or more of the group consisting of divinylbenzene, ethylene glycol dimethylacrylate, bisphenol A dimethacrylate, N,N'-methylenebis(acrylamide), bisphenol A epoxy acrylate, bisphenol diacrylate, tripropylene glycol diacrylate, propoxylated neopentyl diacrylate, propoxylated glycerol diacrylate, pentaerythritol propoxylate triacrylate, butandiol dimethacrylate, tricyclodecane dimethanol diacrylate, pentaerythritol triacrylate, ditrimethylolpropane tetraacrylate, dipentaerythritol penta/hexa-acrylate, tripropylene diacrylate, trimethylol propane ethoxylate triacrylate, trimethylol propane propoxylate triacrylate, di(trimethylolpropane) tetraacrylate, glycerol propoxylate triacrylate, poly(ethylene glycol) diacrylate, poly (propylene glycol) diacrylate, and tri(propylene glycol) diacrylate, for example the crosslinking monomer is selected from one or more of the group consisting of divinylbenzene, ethylene glycol dimethylacrylate, bisphenol A dimethacrylate, and N,N'-methylenebis(acrylamide); and/or (b) a solvent. For example, the solvent may be selected from one or more of the group consisting of 1,4-dioxane, tetrahydrofuran, diglyme, ethyl acetate, butyl acetate, acetone, methyl ethyl ketone, and water.

The second functional monomer discussed above may be selected from one or more of the group consisting of one or more of the group consisting of acrylic acid, methacrylic acid, 2-carboxyethyl acrylate, acrylamide, methacrylamide, allylamine, (hydroxyethyl)methacrylate, hydroxypropyl methacrylate, 4-hydroxybutyl acrylate, glycidyl methacrylate, allyl glycidyl ether, 1,2-epoxy-5-hexene, maleic anhydride, 2-hydroxyethyl methacrylate, and 2-carboxyethyl acrylate oligomers.

In the process above:

(a) the polymerization of the first and/or second step may be conducted at a temperature of from 30 to 80° C., such as from 50 to 70° C.; and/or (b) the total polymerization time for the first and second step may be from 10 to 30 hours, such as from 16 to 24 hours.

In order to conduct the process described above, one needs to provide monodisperse superparamagnetic precursor beads. These beads may be formed by a process that comprises:

(i) providing naked monodisperse superparamagnetic beads, which comprise a core portion formed from a polystyrene polymeric matrix material, where the polystyrene polymeric matrix material encapsulates a first batch of superparamagnetic $Fe_3O_4$ nanoparticles;

a first shell portion located directly on top of the core portion and formed from a crosslinked polymeric matrix material that is formed from a styrene monomer, a crosslinking monomer and a first functional monomer that has functional groups, where the copolymeric matrix material encapsulates a second batch of superparamagnetic $Fe_3O_4$ nanoparticles; and a second shell portion located directly on top of the first shell portion, which comprises superparamagnetic $Fe_3O_4$ nanoparticles which is bound to the functional groups on a surface of the first shell portion; and (ii) forming the monodisperse superparamagnetic precursor beads by forming polymeric precursor anchor points on the first shell portion by reacting the naked monodisperse superparamagnetic beads with an anchoring material selected from one or more of the group consisting of methacryloyl chloride, 3-ethoxyacryloyl chloride, acryloyl chloride, 4-pentenoyl chloride, methacrylic anhydride, 4-pentenoic anhydride, crotonic anhydride, valeric anhydride, 10-undecenoyl chloride, glycidol methacrylate, glycidol, and allyl glycidyl ether.

The naked monodisperse superparamagnetic beads may be formed by a process that comprises:

(ai) providing monodisperse beads, which comprise:

a core portion formed from a polystyrene polymeric matrix material; and a first shell portion located directly on top of the core portion and formed from a crosslinked polymeric matrix material that is formed from a styrene monomer, a crosslinking monomer and a first functional monomer that has functional groups; and (aii) forming the naked monodisperse superparamagnetic beads by placing the monodisperse beads into a solution that comprises a Fe(III) salt and a Fe(II) salt and adding a base.

In the process described directly above:

(a) the Fe(III) salt may be selected from $FeCl_3$ and/or $Fe_2(SO_4)_3$; and/or (b) the Fe(II) salt may be selected from one or more of the group consisting of $FeCl_2$, $FeSO_4$, $Fe(OAC)_2$; and/or (c) the base may be selected from one or more of the group consisting of ammonia hydroxide, NaOH, KOH, and amine; and/or (d) the solution may further comprise $CoCl_2$ and/or $MnCl_2$.

The monodisperse beads mentioned above may be formed by a "one-pot three-stage" continuous process, which process comprises:

(a) in a first stage, generating a polystyrene core by dispersion polymerization of a styrene monomer with an initiator and a polymer stabilizer in a mixture of alcohol with water to form nucleated polystyrene cores;

(b) in a second stage, adding a crosslinking monomer to mixture comprising nucleated polystyrene cores; and (c) in a third stage adding a first functional monomer to the material obtained from the second stage to provide the monodisperse beads, optionally wherein the polystyrene beads are generated in situ, and the subsequent addition of crosslinker and functional monomers do not cause a second nucleation, thus leading to spherical monodisperse copolymer beads of (styrene/crosslinker/functional monomer) bearing functional groups on a surface.

In the process directly above:

(a) the initiator may be selected from an azo initiator, optionally wherein the azo initiator is selected from one or more of the group consisting of 2,2'-azobis(2-methylpropionitrile) (AIBN), and 2,2'-azobis(2-methylbutyronitrile) (AMBN); and/or (b) the polymer stabilizer may be selected from one or more of the group consisting of poly(vinylpyrrolidone) (PVP), polyethylenimine (PEI), polyacrylic acid (PAA), polyvinyl alcohol (PVA), hydroxypropyl methylcellulose (HPC), and chitosan; and/or (c) the styrene monomer may be selected from one or more of the group consisting of styrene, and a styrene derivative, optionally wherein the styrene derivative is selected from one or more of the group consisting of 4-methylstyrene, 3-methylstyrene, and 4-tertbutylstyrene; and/or (d) the alcohol may be selected from one or more of the group consisting of methanol, ethanol, isopropanol, or a mixture of them; and/or (e) the volume ratio of alcohol to water may be from 1:1 to 40:1, such as from 2:1 to 20:1.

The crosslinking monomer used above may be selected from one or more of the group consisting of divinylbenzene, ethylene glycol dimethylacrylate, bisphenol A dimethacrylate, butanediol dimethacrylate, tricyclodecane dimethanol diacrylate, pentaerythritol triacrylate, tripropylene glycol diacrylate, propoxylated neopentyl diacrylate, pentaerythritol triacrylate, ditrimethylolpropane tetraacrylate, dipentaerythritol pentaacrylate, dipentaerythritol penta/hexa-acrylate, tripropylene diacrylate, trimethylol propane ethoxylate triacrylate, trimethylol propane propoxylate triacrylate, di(trimethylolpropane) tetraacrylate, glycerol propoxylate triacrylate, pentaerythritol propoxylate triacrylate, poly(ethylene glycol) diacrylate, poly(propylene glycol) diacrylate, and tri(propylene glycol) diacrylate, optionally wherein the crosslinking monomer is selected from one or more of the group consisting of divinylbenzene, ethylene glycol dimethylacrylate, bisphenol A dimethacrylate, and N,N'-methylenebis(acrylamide).

The functional groups on the first functional monomer may independently be selected from one or more of amino, carboxyl, epoxy, and hydroxyl. For example, the functional groups on the functional monomer in the first shell portion and the second layer of the second shell portion may independently be selected from a combination of hydroxyl and carboxyl groups or a combination of amino and carboxyl groups. More specifically, the first functional monomer may be selected from one or more of the group consisting of acrylic acid, methacrylic acid, 2-carboxyethyl acrylate, acrylamide, methacrylamide, allylamine, (hydroxyethyl)methacrylate, hydroxypropyl methacrylate, 4-hydroxybutyl acrylate, glycidyl methacrylate, allyl glycidyl ether, 1,2-epoxy-5-hexene, maleic anhydride, 2-hydroxyethyl methacrylate, and 2-carboxyethyl acrylate oligomers.

In the process directly above, the weight ratio of the styrene monomer to cross-linker may be from 20:1 to 1:2, such as from 10:1 to 1:1. For example, the weight ratio of the styrene monomer to first functional monomer is between 20:1 to 1:2, preferably between 10:1 to 1:1.

Before the monodisperse beads are used, they are washed with one or more solvents before use in a subsequent process step. The solvent used for washing may be selected from one or more of the group consisting of water, methanol, ethanol, isopropanol, and THF.

In the processes described above, the resulting monodisperse superparamagnetic beads may have:

(a) a coefficient of variation based on their diameter of less than 15%, such as less than 10%, such as less than 5%, such as less than or equal to 2%; and/or (b) an average diameter of from 0.2 to 5.0 microns, such as from 0.5 to 4.0 microns.

The current invention relates to monodisperse superparamagnetic beads useful for in-vitro diagnostic (IVD) assays and other applications. These monodisperse superparamagnetic beads have a polystyrene core, covered by a crosslinked layer of styrene-crosslinker-functional monomer, and further covered by a layer of superparamagnetic $Fe_3O_4$ nanoparticles with little portion dispersed inside the polymer matrix. Lastly, a functional coating is fabricated on the beads surface to bind and cover the superparamagnetic $Fe_3O_4$ nanoparticles, as well as providing functional groups for IVD assays.

Thus, as will be appreciated, the superparamagnetic beads described herein may be used in IVD assays.

Advantages of the invention are described below.

Highly monodisperse superparamagnetic beads are produced.

The highly monodisperse copolymer beads comprising of three monomers [styrene, crosslinker (for example DVB), functional monomer] are produced by a "one-pot three-stage" polymerization procedure. This procedure is simple and practical compared to the state-of-the-art procedure that requires multi-step synthetic process involving cumbersome operations and consuming much longer polymerization time.

In the a "one-pot three-stage" polymerization procedure, each monomer plays are role. (a) styrene provides nucleation template, leading to spherical monodisperse beads; (b) crosslinker, such as DVB provides crosslinking, making the beads stiffer and tolerant to organic solvents; and (c) the functional monomer facilitates the upload of superparamagnetic nanoparticles (NPs).

The obtained copolymer beads of three monomers (styrene, crosslinker, functional monomer) are spherical and highly monodisperse, the beads diameter can be tuned by regulating the polymerization factors, such as the initiator concentration, PVP concentration, loading amount of monomers.

Various functional monomers can be copolymerized into the beads to introduce functional groups on the beads surface. Such functional monomers include 2-carboxyethyl acrylate, acrylic acid, allylamine, 1-vinyl imidazole, 4-vinyl pyridine. In addition, more than one kind of functional monomers may be added together at the third stage to introduce multiple functional groups in one process.

The density of functional groups on beads surface can be fine-tuned by regulating the loading amount of the functional monomers.

After the completion of nucleation of polystyrene, the subsequent addition of crosslinker (such as DVB) and functional monomers do not cause the second nucleation, which is one of the reasons for the production of highly monodisperse beads.

High loading of superparamagnetic $Fe_3O_4$ NPs (e.g. 30-50 wt %) on beads can be achieved by on-site generation of NPs.

The size of $Fe_3O_4$ NPs formed on the surface are well-controlled due to the well-controlled functional group grafting on the PS core.

Further aspects and embodiments of the invention will be described by reference to the following non-limiting examples.

EXAMPLES

The current invention relates to a monodisperse superparamagnetic beads having a core-shell structure. The beads may be made by a four-step process outlined in FIG. 2, which is fundamentally different from the conventional synthetic methods for the production of monodisperse superparamagnetic beads.

Details of the four steps are further described in detail below with reference to FIG. 2.

Step 1: Synthesis of Highly Monodisperse Terpolymer Beads from Three Monomers (Styrene, Crosslinker, Functional Monomer) Via a "One-Cot Three-Stage" Polymerization Procedure (a) The first stage is a dispersion polymerization of styrene in ethanol containing from 0 to 20 v % water. Nucleation is completed in this step to give a polystyrene core 20. Most of the styrene monomers (such as 60-80 wt %) is consumed, thus the number of beads is fixed in this stage. The polymerization time is between 2-12 hours, preferably between 4-10 hours.

(b) The second stage is cross-linking by addition of crosslinker. A core-shell structure (A) is formed by the copolymerization of crosslinker with the rest of styrene. The polymerization time is between 1-8 hours, preferably between 2-6 hours.

(c) In the third stage, a functional monomer is added to copolymerize with the remaining small amount of crosslinker and styrene. The resulting terpolymer shell 40 contains hydrophilic functional groups on the bead surface. In addition, more than one functional monomers (such as two or three functional monomers) can be added together at this stage, which introduces multiple functional groups in one run. The polymerization time is between 8-24 hours, preferably between 10-20 hours.

It is surprisingly found that the "one-pot three-stage" continuous process is able to produce spherical highly monodisperse terpolymer beads from three monomers (styrene, DVB and functional monomer). This "one-pot three-stage" continuous process has three outstanding features:

(a) Styrene provides a nucleation template, leading to spherical monodisperse beads.

(b) The crosslinker (such as DVB) provides crosslinking and determines the bead stiffness and tolerance to organic solvents.

(c) The functional monomer introduces hydrophilic functional groups, such as —COOH, —$NH_2$, epoxy group, acid anhydride groups, which can be further modified to facilitate the uploading of superparamagnetic $Fe_3O_4$ NPs.

It is also surprisingly found that the addition of crosslinker and the functional monomer do not cause second nucleation. In addition, the addition of functional monomer in this stage achieves a high density of functional groups on the surface which enables in-situ precipitation of the superparamagnetic $Fe_3O_4$ NPs.

Step 2: Washing and Surface Modification of the as-Synthesized Terpolymer Beads with Organic Solvents The as-synthesized terpolymer beads (A) from step 1 are thoroughly washed with organic solvents. The aim of washing is to remove unreacted styrene, crosslinker and functional monomers, as well as stabiliser, such as PVP in the solution. In addition, washing with polar solvents (examples below) can also remove some of the linear polystyrene present in the polymer matrix, which may loosen the beads and generate some pores (depicted as 30) to benefit the on-site loading of superparamagnetic $Fe_3O_4$ NPs. The washed beads are redispersed and stored in water to give (B).

During the washing or soaking process, the functional groups on the beads surface can be further modified to facilitate the uploading of superparamagnetic $Fe_3O_4$ NPs. When epoxy groups are introduced to beads surface, the epoxy groups may undergo ring-opening hydrolysis, ring-opening aminolysis, or ring-opening polymerization to further modify the bead surface.

Step 3: On-Site Generation and Upload Superparamagnetic $Fe_3O_4$ NPs on Terpolymer Beads The washed beads (B) are dispersed into an aqueous solution (mixture of water and polar solvent such as THF) containing $Fe^{3+}$ and $Fe^{2+}$ in 2:1 molar ratio, and the dispersion is heated (to e.g. 70° C.) with stirring for several hours to allow the two ions to interact with the functional groups of the beads. Without wishing to be bound by theory, it is believed that during this process some $Fe^{3+}$ and $Fe^{2+}$ ions will penetrate into the beads polymer matrix while some will be adsorbed on the beads surface. Then aqueous ammonia is added to transform the $Fe^{3+}$ and $Fe^{2+}$ ions to $Fe_3O_4$ nanoparticles ($Fe_3O_4$ NPs; 60). After the addition of aqueous ammonia, ligands to stabilize $Fe_3O_4$ NPs, such as polyacrylic acid or tartaric acid or citric acid may be added to the beads solution to assist the formation of superparamagnetic $Fe_3O_4$ NPs. The obtained superparamagnetic polymer beads (C) are separated by centrifugation and washed with water and methanol to remove the loose $Fe_3O_4$ NPs 60.

Step 4: Fabrication of Functional Coating on Superparamagnetic Beads.

A coating layer 80 is fabricated on superparamagnetic polymer beads (C). The coating layer is achieving by reacting an anchoring material with (C), followed by free radical polymerization of a bulk monomer, a second functional monomer and optionally crosslinkers. Functional groups such as hydroxyl group, carboxyl group can be further introduced on the surface with required density.

In a specific example, the superparamagnetic $Fe_3O_4$ NPs 40 are encapsulated within the functional polymeric network formed from step 2. To achieve polymer grafting, an anchoring material is introduced through reaction with the functional groups remaining on the beads surface in step 2, for example, the hydroxyl group or amine group. The anchoring material can be chosen from listed in the detailed description. An anhydrous solvent is chosen from 1,4-dioxane, tetrahydrofuran, diglyme, ethyl acetate, butyl acetate, acetone, methyl ethyl ketone. Preferably, tetrahydrofuran and diglyme. The reaction time is 12-36 hrs with inert gas purging. The resulting beads are washed with organic solvent to remove excess monomers.

The coating layer is further grafted by reacting the anchoring group (such as an unsaturated group) on the beads surface with a bulk monomer in a first step and a second functional monomer in a second step, and optionally with a crosslinker. The specific materials are listed in detailed description. At this stage, the polymerization time is between 10-30 hours, preferably between 16-24 hours. The free-radical polymerization can be carried at a temperature between 40-80° C., preferably between 50-70° C.

Materials

The materials were purchased from the sources as provided below.

Styrene: Tokyo Chemical Industry (TCI), stabilized with TBC (4-tert-butylcatechol), >99.0% (GC).

Azobisisobutyronitrile (AIBN): Sigma-Aldrich (12 wt % in acetone).

Sodium persulfate ($Na_2S_2O_8$, SPS): Alfa Aesar, crystalline, 98%.

Polyvinylpyrrolidone (PVP, K30, MW=40,000): TCI, total nitrogen 12.0% to 12.8% (calcd. on anhydrous substance); water max. 7.0%, K value 26.0 to 34.0.

Divinylbenzene (DVB, m- and p-mixture): TCI, 50.0% (GC) (contains ethylvinylbenzene, diethylbenzene) (stabilized with 4-tert-butylcatechol).

Acrylic acid: TCI, >99.0% (GC) (stabilized with monomethyl ether hydroquinone).

Glycidyl methacrylate: Sigma-Aldrich, 297.0% (GC).

2-hydroxyethyl methacrylate: Sigma-Aldrich, 299.0%

2-carboxyethyl acrylate oligomers: Sigma-Aldrich, 2000 ppm MEHQ as inhibitor.

Ethanol: 99%.

Citric acid: Sigma-Aldrich, 98%.

Trimethylolpropane triacrylate: Sigma-Aldrich

Methyl methacrylate: TCI 2-(2-Aminoethoxy)ethanol: Sigma-Aldrich, 98%;

Deionized (DI) water obtained from ELGA Ultrapure Water Treatment Systems (PURELAB Option).

Scanning electron microscope (SEM) imaging was performed using a JEOL JSM 6700F.

Transmission electron microscopy (TEM) imaging was performed using a JEOL 2100F.

Mechanical stirrer Wiggens, WB2000-M overhead stirrer.

Thermal Gravimetric Analysis (TGA) was performed using Shimadzu, DTG-60. Samples with about 15 mg (dry mass) of beads were dried at 70° C. in the oven. The empty crucibles, including the reference crucible and the sample crucible, were places on the holder in parallel. The weight difference between the reference crucible and the sample crucible was eliminated. The beads sample was then filled into the sample crucible. The temperature profile was set from room temperature to 700° C. by the increment of 20° C./min and with 10 min holding time at 100° C. The whole process was under $N_2$ purge. The magnetic content was calculated by the following equation:

Fe %=$W_2/W_1\times100\%$, where $W_1$ is the weight at 100° C. after holding for 10 min and $W_2$ is the weight at 700° C.

Measurement of superparamagnetic property was conducted with 6000 PPMS (Physical Property Measurement System) of Quantum Design. Samples with about 15 mg (dry mass) of beads were dried in a vacuum oven under room temperature. The magnetization curves [M-H] was obtained using a physical property measurement system (Quantum Design, PPMS 6000) equipped with a vibrating sample magnetometer (P525) and a vibrating sample magnetometer (Micro Sense, EV9). M-H was measured at 300 K with an applied field of appropriate strength.

Coefficient of variation (CV) % of the polystyrene beads was calculated from SEM image (×10,000) measurement. 100 of beads were measured for by using IMAGE J and the mean diameter and CV were calculated.

General Considerations

Mechanical stirring (200 rpm) was used for all the polymerization processes. Prior to use, DI water and ethanol were bubbled with nitrogen for 20 min to remove oxygen. All the chemicals (including AIBN, SPS, PVP, acrylic acid, allyl amine, DVB, styrene, glycidol, glycidyl methacrylate, bisphenol A diglycidylether and 2-hydroxyethyl methacrylate) were used as received without purification. All the polymerizations and reactions were carried out under the protection of nitrogen using standard Schlenk line techniques.

Example 1

Synthesis of Monodisperse Beads Bearing —COOH and —OH Groups

Described below is a “one-pot three-stage” polymerization process to synthesize monodisperse beads bearing —COOH and —OH groups.

Figure 3:
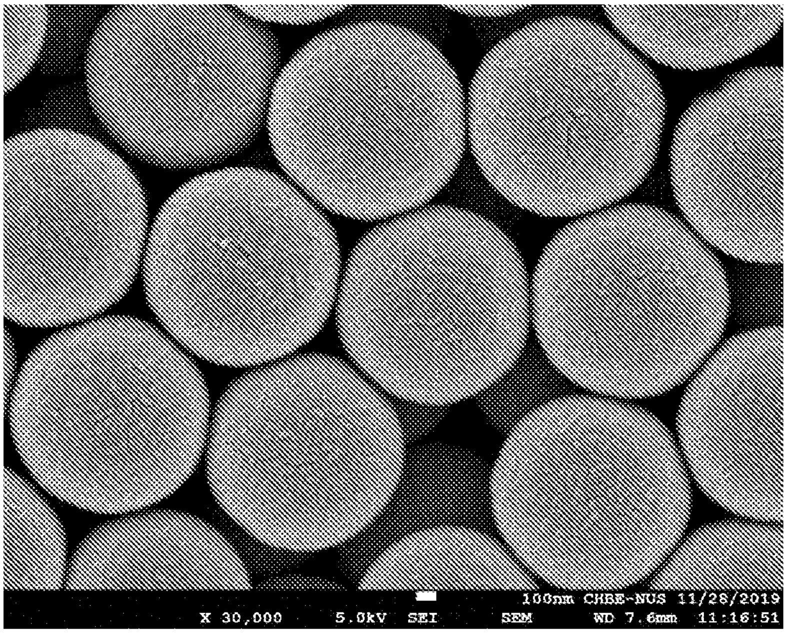
FIG. 3 depicts a SEM image of A-1.

To a 250 mL three-necked round bottom glass reactor equipped with a mechanical stirrer, AIBN solution (2 g, 12 wt % in acetone) was added and nitrogen was introduced from one side-neck to remove acetone solvent. After 10 minutes of nitrogen flow, dried AIBN powder was observed at the bottom of the reactor. Then PVP (0.2 g), ethanol (80 mL), and DI water (20 mL) were added. The mixture was stirred at room temperature for 5 minutes to obtain a clear solution, which was then heated to 60° C. with an oil bath, followed by addition of styrene (7.5 mL). A white colloidal solution was generated after 4 hours, indicating polymerization of styrene. A solution of DVB (3 mL DVB in 7 mL ethanol) was then slowly added with a constant pressure dropping funnel over 30 minutes. After addition of DVB solution was completed, the reaction (cross-linking polymerization) was continued for 3 hours. Then a monomer solution of 2-hydroxyethyl methacrylate (0.75 g in 5 mL ethanol) and 2-carboxyethyl acrylate oligomers (0.75 g in 5 mL ethanol, neutralized with ammonia solution, 25% W/W) was added with a syringe. The reaction (polymerization) was continued for 6 hours to give a milk-like colloidal solution. SEM images showed that the as-synthesized beads were spherical and monodisperse, bearing a diameter of ~1.0 micron (FIG. 3). The obtained beads were named as "A-1".

Example 2

Washing and Surface Modification of Beads A-1

The beads of A-1 (50 mL dispersion, mass concentration ~8 wt %) was isolated by centrifugation and re-dispersed in ethanol by sonication. The beads were washed with ethanol (50 mL×2) and a mixture of THF and water (1:1 volume ratio; 50 mL×2). The obtained beads were centrifuged and re-dispersed in THF (50 mL) to give B-1. SEM image showed that the beads were spherical and monodisperse with a diameter of ~1.0 micron.

Example 3

Magnetization of Beads B-1

Figure 4:
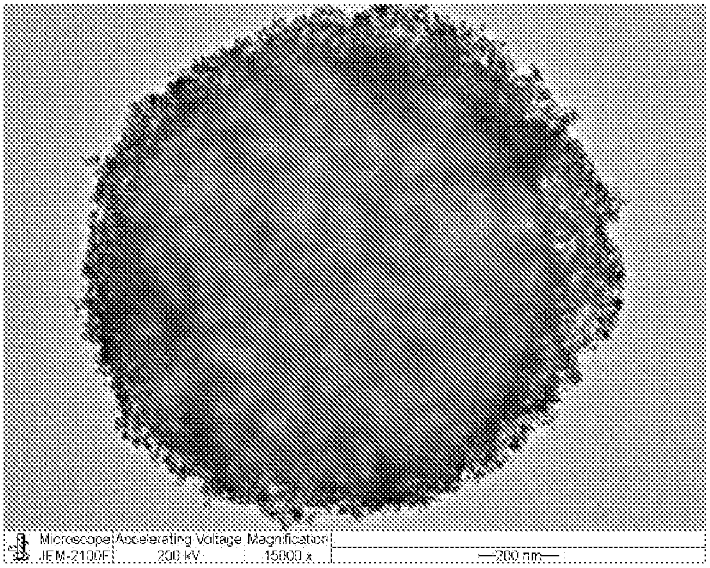
FIG. 4 depicts a TEM image of C-1
Figure 5:
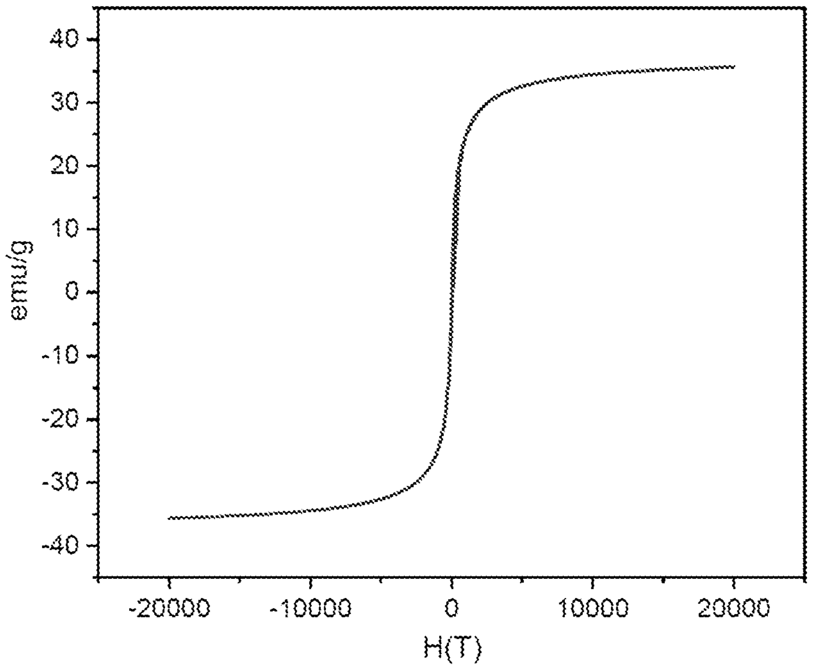
FIG. 5 depicts a hysteresis curve for C-1.

To a 250 mL three-necked round bottom glass reactor equipped with a mechanical stirrer, $FeCl_3$ (8.0 g) and 100 mL water were added and stirred to form a brown solution, followed by addition of $FeCl_2$ (3.1 g), and THF (20 mL). The mixture was stirred for 30 min to form a solution, to which a solution of beads B-1 in water (50 mL, mass concentration ~8 wt %) was added and stirred at 70° C. for 3 hours. After the mixture was cooled to room temperature, aqueous ammonia (25 wt %, 30 mL) was added under vigorous stirring, affording a black slurry immediately. A citric acid solution (0.5 g, in 10 mL water) was added into the reactor and the black slurry was heated to 70° C. for 1 hour to complete the reaction. The superparamagnetic beads were purified with several centrifugal shifts to remove unbound superparamagnetic NPs, and finally re-dispersed into DI water (100 mL, ~4 wt %). The obtained black-brown superparamagnetic beads were named as "C-1". TGA result showed that the beads contained 43 wt % NPs. The obtained magnetic beads are monodisperse with some $Fe_3O_4$ NPs scattered homogenously within the core and with a very thick layer of fluffy $Fe_3O_4$ NPs on the surface. The thickness of $Fe_3O_4$ NPs layer is about 70-100 nm around the beads (FIG. 4). The superparamagnetic property was measured by using 6000 PPMS (Physical Property Measurement System) of Quantum Design. The saturation magnetization (MS) values were normalized by using the mass of beads as determined by atomic absorption spectroscopy. FIG. 5 shows typical hysteresis curves at room temperature for sample C-1. The hysteresis loop indicates a superparamagnetic behavior as evident by zero coercivity and remanence on the magnetization loop.

Example 4

Fabrication of Functional Coating

Binding step: To a 250 mL three-necked round bottom glass reactor equipped with a mechanical stirrer, superparamagnetic beads C-1 (30 mL, 4 wt % in anhydrous THF), methacryloyl chloride (100 mg, dissolved in 10 mL anhydrous THF) were added. The mixture was heated to and maintained at 60° C. for 18 hours under nitrogen purge, which was then cooled to room temperature. The beads were washed with THF to remove excess methacryloyl chloride and then with water. The beads were stored in water under nitrogen protection.

Figure 6:
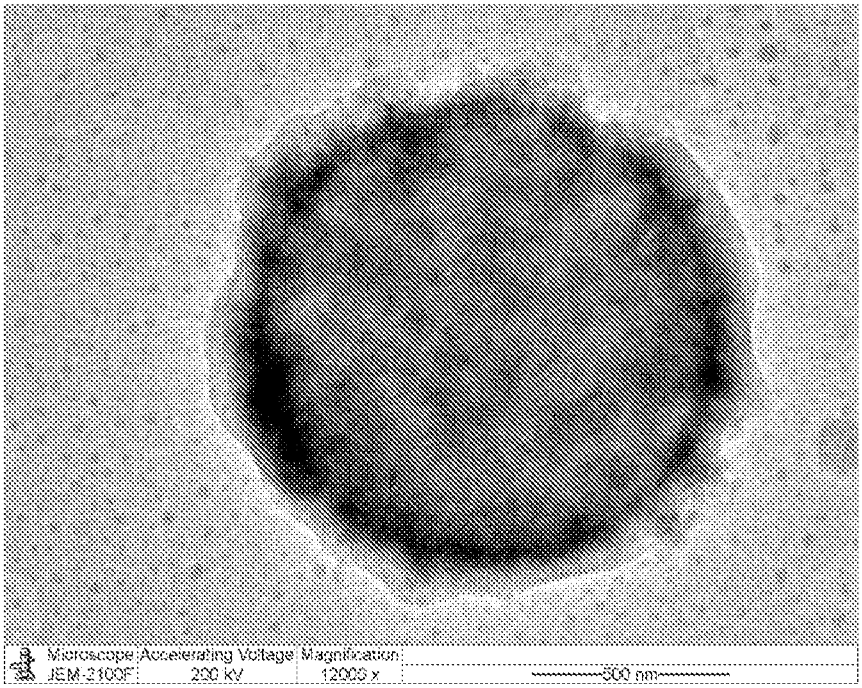
FIG. 6 depicts a TEM image of D-1.

Coating step by emulsion polymerization: The modified superparamagnetic beads from the previous step (10 mL, ~4 wt % in water) were added to a 50 mL centrifuge tube containing 30 mL DI water. The mixture was then added to a 250 mL three-necked round bottom glass reactor equipped with a mechanical stirrer. The reactor was flushed with nitrogen to remove oxygen, then SPS (30 mg, dissolved in 2 mL water) was added. The mixture dispersion was heated to and stirred at 60° C. for 10 minutes. Subsequently, a mixture of monomers containing methyl methacrylate (400 mg), trimethylolpropane triacrylate (200 mg), was added in 4 batches over a 1-hour period (and therefore at 20-minute intervals). After addition of the monomer mixture was completed, the reaction (coating polymerization) was continued for 6 hours at 60° C. After cooling to room temperature, the coated superparamagnetic beads were isolated with a magnetic separator and washed with ethanol (50 mL×2) and DI water (50 mL×2). The coated superparamagnetic beads were named as D-1. The TEM image in FIG. 6 clearly shows that the structure of beads corresponds to those proposed in FIG. 2(D). The edge of the beads was fully covered by a layer of polymer which can prevent magnetic particles from leaching out.

Example 5

Synthesis of Monodisperse Beads Bearing Epoxy Groups

Described below is a "one-pot three-stage" polymerization process to synthesize monodisperse beads made from three monomers (styrene, DVB, GMA), the beads bearing epoxy groups.

To a 250 mL three-necked round bottom glass reactor equipped with a mechanical stirrer, AIBN solution (2.0 g, 12 wt % in acetone) was added, and nitrogen was introduced from one side-neck to remove acetone solvent. After 10 minutes of nitrogen flow, dried AIBN powder was observed at the bottom of the reactor. Then PVP (0.3 g), ethanol (80 mL), and DI water (16 mL) were added. The mixture was stirred at room temperature for 5 minutes to obtain a clear solution, which was then heated to 60° C. with an oil bath, followed by addition of styrene (7.5 mL).

Figure 7:
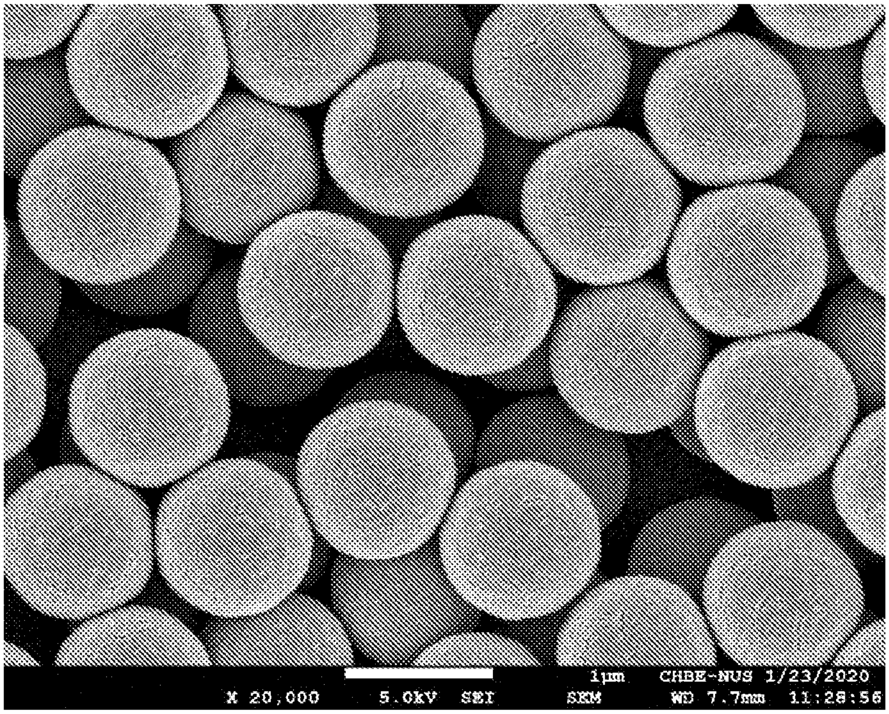
FIG. 7 depicts a SEM image of A-2.

A white colloidal solution was generated after 6 hours, indicating polymerization of styrene, A solution of DVB (1.5 mL, dissolved in 8.5 mL of ethanol) was then slowly added with a constant pressure dropping funnel over 30 minutes. After addition of DVB solution was completed, the reaction (cross-linking polymerization) was continued for 2 hours. Then a solution of glycidyl methacrylate (GMA) (2.0 g, dissolved in 10 mL ethanol) was added with a syringe. The reaction (polymerization) was continued was for 24 hours to give a milk-like colloidal solution. SEM images showed that the as-synthesized beads were spherical and monodisperse, bearing a diameter of ~1.0 micron (FIG. 7). The obtained beads were named as "A-2".

Example 6

Washing and Surface Modification of A-2

The beads dispersion of A-2 (50 mL, mass concentration ~8 wt %) was isolated by centrifugation and re-dispersed in ethanol by sonication. The beads were washed with ethanol (50 mL×2) and mixture of THF and water (1:1 volume ratio; 50 mL×2), The beads were re-dispersed in a THF solution containing 1 g of 2-(2-aminoethoxy)ethanol, and stirred at room temperature for 20 hours. The beads were then washed with water 5 times and redispersed in water to give B-2. SEM image showed that the beads were spherical and monodisperse with a diameter of ~1.0 micron.

Example 7

Magnetization of B-2 Beads

Figure 8:
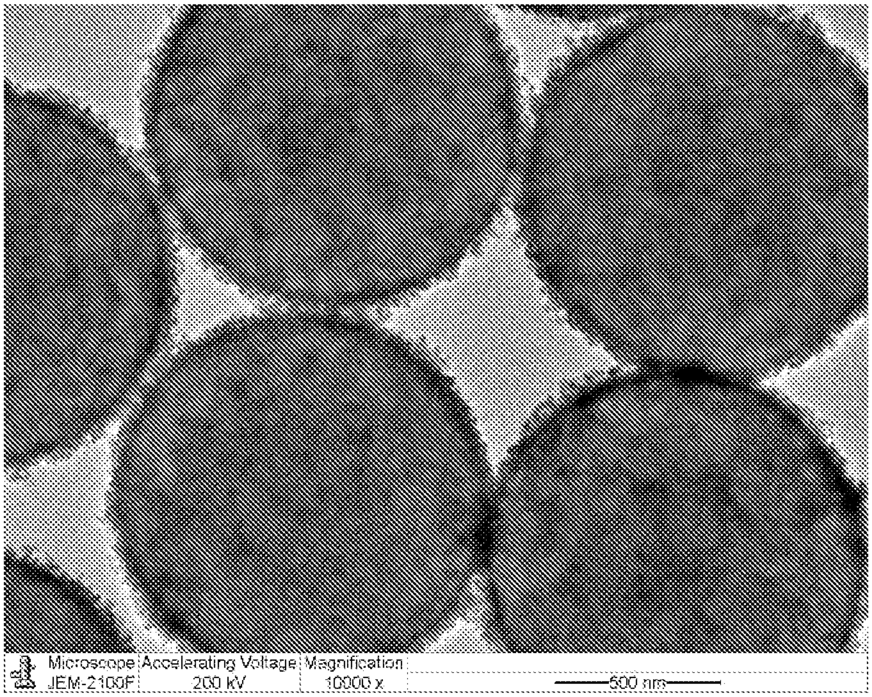
FIG. 8 depicts a TEM image of C-2.

To a 250 mL three-necked round bottom glass reactor equipped with a mechanical stirrer, $FeCl_3$ (8.0 g) and 100 mL water were added and stirred to form a brown solution, followed by addition of $FeCl_2$ (3.1 g), and THF (20 mL). The mixture was stirred for 30 min to form a solution, to which a solution of beads B-2 (50 mL, mass concentration ~8 wt % in water) was added and stirred at 65° C. for 3 hours. After the mixture was cooled to room temperature, aqueous ammonia (25 wt %, 25 mL) was added under vigorous stirring, affording a black slurry immediately. A citric acid solution (0.5 g, in 10 mL water) was added into the reactor and the black slurry was heated to 70° C. for 1 hour to complete the reaction. The superparamagnetic beads were purified with several centrifugal shifts to remove unbound superparamagnetic NPs, and finally re-dispersed into DI water (100 mL, ~4 wt %). The obtained black-brown superparamagnetic beads were named as "C-2". TGA result showed that the beads contained 41 wt % NPs. The TEM image of C-2 is shown in FIG. 8.

Example 8

Fabrication of Functional Coating

Binding step: To a 250 mL three-necked round bottom glass reactor equipped with a mechanical stirrer, superparamagnetic beads C-2 (10 mL, 4 wt % in anhydrous THF), methacrylic anhydride (120 mg, dissolved in 30 mL anhydrous THF) and triethylamine (TEA) (20 μL, dissolved in 10 mL anhydrous THF) were added. The mixture was heated to and maintained at 65° C. for 3 hours under nitrogen purge, which was then cooled to room temperature. The beads were washed with THF to remove excess methacrylic anhydride and then with water. The beads were stored in water under nitrogen protection.

Figure 9:
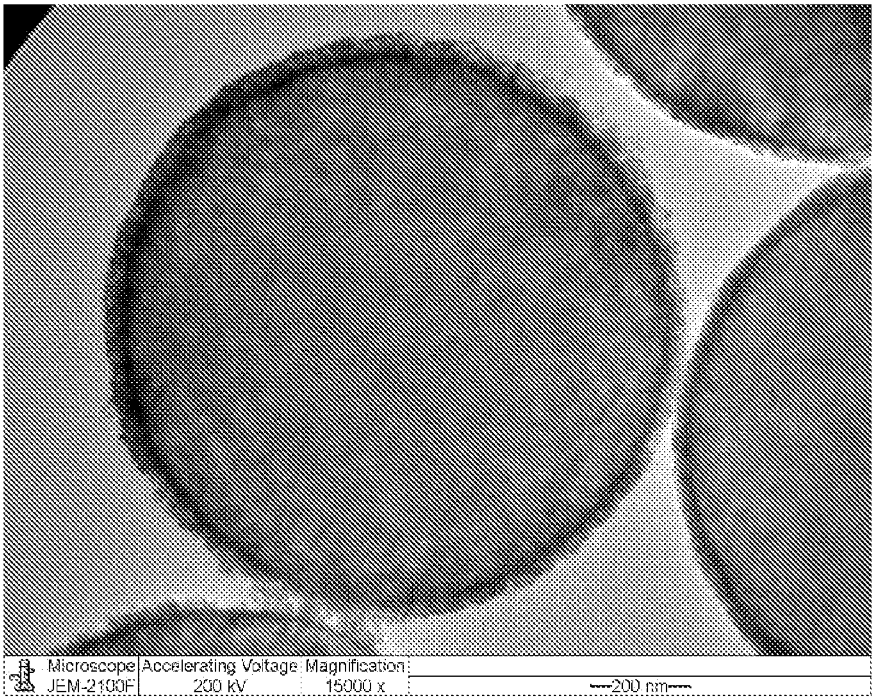
FIG. 9 depicts a TEM image of D-2.

Coating stop by grafting polymerization: The modified superparamagnetic beads from the previous step (10 mL, ~4 wt % in water) were added to a 50 mL centrifuge tube containing 30 mL DI water. The mixture was then added to a 250 mL three-necked round bottom glass reactor equipped with a mechanical stirrer. The reactor was flushed with nitrogen to remove oxygen, then SPS (30 mg, dissolved in 2 mL water) was added. The mixture dispersion was heated to and stirred at 60° C. for 10 minutes. Subsequently, a mixture of monomers containing methyl methacrylate (400 mg), bisphenol A epoxy acrylate (150 mg), was added in 4 batches (interval 1 h) over a period of 4 hours. After addition of the monomer mixture was completed, the reaction (coating polymerization) was continued for 4 hours at 60° C. Acrylic acid monomers (100 mg diluted in water further neutralized with ammonia solution, 25% (w/w).) was added and reaction was continued for 16 hours at 60° C. After cooling to room temperature, the coated superparamagnetic beads were isolated with a magnetic separator, and washed with ethanol (50 mL×2), DI water (50 mL×2). The coated superparamagnetic beads were named as D-2. TEM image in FIG. 9 shows a smoother outer layer as compared with that of C-1, indicating that the nanoparticles have been effectively encapsulated within the polymeric network.

Comparative Example 1

Synthesis of Monodisperse Beads without Functional Groups

Described below is a "one-pot two-stage" polymerization process to synthesize monodisperse beads of two monomers (styrene-DVB) without functional groups.

To a 250 mL three-necked round bottom glass reactor equipped with a mechanical stirrer, AIBN solution (2.2 g, 12 wt % in acetone) was added, and nitrogen was introduced from one side-neck to remove acetone. After 10 minutes of nitrogen flow, dried AIBN powder was observed at the bottom of the reactor. Then PVP (0.9 g), ethanol (90 mL), and DI water (10 mL) were added. The mixture was stirred at room temperature. for 5 minutes to obtain a clear solution, which was then heated to 70° C. with an oil bath followed by addition of styrene (7.5 mL).

Figure 10:
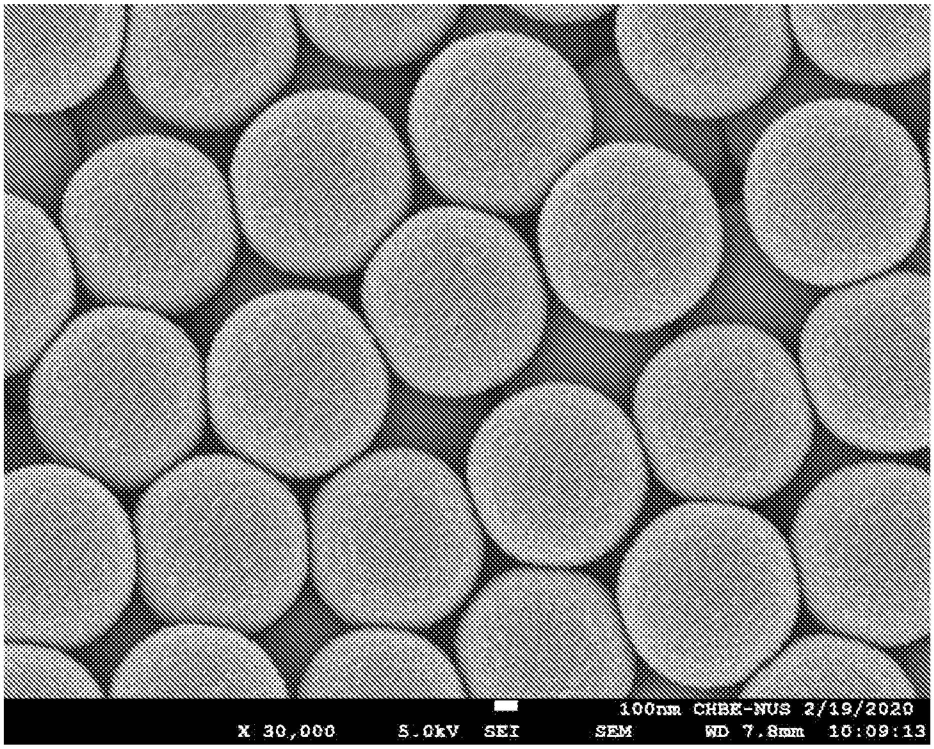
FIG. 10 depicts a SEM image of CE-2.

A white colloidal solution was generated after 6 hours, indicating polymerization of styrene. A solution of DVB (1.5 mL, dissolved in 8.5 mL of ethanol) was then added slowly with a constant pressure dropping funnel over 30 minutes. After addition of DVB solution was completed, the reaction (cross-linking polymerization) was continued for 20 hours to give a milk-like colloidal solution. SEM images showed that the as-synthesized beads were spherical and monodisperse, bearing a diameter of ~0.8 micron (FIG. 10). The obtained beads were named as "CE-1". Because no functional monomers were added, beads CE-1 has no functional groups on surface, the beads are hydrophobic.

Comparative Example 2

Washing and Soaking of CE-1

The as-synthesized poly(styrene-DVB) beads of CE-1 (50 mL dispersion, mass concentration ~8 wt %) was isolated by centrifugation and re-dispersed into ethanol by sonication. The beads were washed with ethanol (50 mL×2) and a mixture of THF and water (1:1 volume ratio; 50 mL×2) and THF (50 mL×2). The washed beads were named as "CE-2". SEM image showed that the beads were spherical and monodisperse with a diameter of ~0.8 micron.

Comparative Example 3

Magnetization of CE-2 Beads

To a 250 mL three-necked round bottom glass reactor equipped with a mechanical stirrer, $FeCl_3$ (8.0 g) and 100 mL water were added and stirred to form a brown solution, followed by addition of $FeCl_2$ (3.1 g), citric acid (8.5 g) and THF (20 mL). The mixture was stirred for 30 min to form a solution, to which a solution of beads CE-2 in THF (50 mL, mass concentration ~8 wt %) was added and stirred at 60° C. for 3 hours. After the mixture was cooled to room temperature, aqueous ammonia (25 wt %, 30 mL) was added under vigorous stirring, affording a black slurry immediately. The black slurry was heated to 60° C. for 1 hour to complete the reaction. The superparamagnetic beads were purified with several centrifugal shifts to remove unbound superparamagnetic NPs, and finally redispersed into DI water (100 mL, ~4 wt %).

Figure 11:
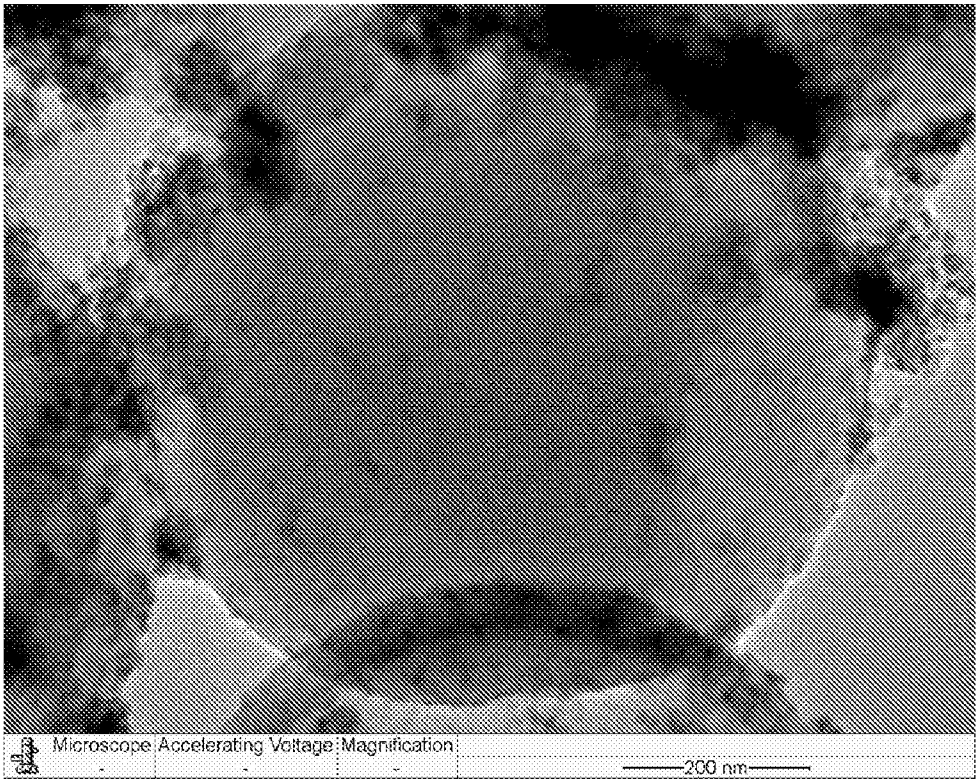
FIG. 11 depicts a TEM image of DE-2.

The obtained beads were still white in color, named as "CE-3". TGA result showed that the beads contained 1 wt % NPs. This comparative experiment showed that poly(styrene-DVB) beads cannot bind sufficient amounts of superparamagnetic $Fe_3O_4$ NPs. This is further confirmed by the TEM image (FIG. 11), which shows that there are only small amounts of magnetic NPs formed on the surface of CE-3. The magnetic nanoparticles only aggregate between the gaps of microspheres.

The invention claimed is:

1. Monodisperse superparamagnetic beads, having a core-shell structure, said bead comprising:

a core portion formed from a polystyrene polymeric matrix material, where the polystyrene polymeric matrix material encapsulates a first batch of superparamagnetic $Fe_3O_4$ nanoparticles;

a first shell portion located directly on top of the core portion and formed from a crosslinked polymeric matrix material that is formed from a styrene monomer, a crosslinking monomer and a first functional monomer that has functional groups, where the copolymeric matrix material encapsulates a second batch of superparamagnetic $Fe_3O_4$ nanoparticles; and a second shell portion located directly on top of the first shell portion, which is formed as a first layer, a second layer and a third layer, the first layer comprises superparamagnetic $Fe_3O_4$ nanoparticles and a first layer polymeric matrix material that comprises a conjugating monomer and a bulk monomer;

a second layer extending beyond the first layer, which is formed from a second layer polymeric material that comprises a bulk monomer; and a third layer on top of the second layer, which is formed from a third layer polymeric material that comprises a bulk monomer and a second functional monomer that has functional groups, wherein:

the superparamagnetic $Fe_3O_4$ nanoparticles in the first layer are directly bound to the functional groups present on an outer surface of the first shell portion;

the first layer polymeric matrix material surrounds the superparamagnetic $Fe_3O_4$ nanoparticles in the first layer; and the second layer polymeric matrix material extends from the first layer polymeric matrix material and forms an outer surface of each monodisperse superparamagnetic bead.

2. The beads according to claim 1, wherein the second and third layer polymeric matrix materials function to prevent the superparamagnetic $Fe_3O_4$ nanoparticles from leaching out when the beads are placed into a solvent.

3. The beads according to claim 1, wherein the functional groups on the functional monomer in the first shell portion and the third layer of the second shell portion are independently selected from one or more of amino, carboxyl, epoxy, and hydroxyl.

4. The beads according to claim 1, wherein the beads have a coefficient of variation based on their diameter of less than 15.

5. The beads according to claim 1, wherein the beads have an average diameter of from 0.2 to 5.0 μm.

6. The beads according to claim 1, wherein the polystyrene polymeric matrix material is formed from one or more of the group consisting of styrene, a styrene derivative, and copolymers thereof.

7. The beads according to claim 1, wherein all of the superparamagnetic $Fe_3O_4$ nanoparticles in a bead account for from 10 to 80 wt % of the entire weight of each bead.

8. The beads according to claim 7, wherein one or more of the following apply:

(a) the first batch of superparamagnetic $Fe_3O_4$ nanoparticles represents from 0.1 to 5 wt % of the entire weight of each bead;

(b) the second batch of superparamagnetic $Fe_3O_4$ nanoparticles represents from 0.5 to 10 wt % of the entire weight of each bead; and (c) the superparamagnetic $Fe_3O_4$ nanoparticles in the first layer of the second shell portion represent from 9.4 to 79.4 wt %, such as from 19.4 to 69.4 wt % of the entire weight of each bead.

9. The beads according to claim 1, wherein the crosslinking monomer is selected from one or more of the group consisting of divinylbenzene, ethylene glycol dimethylacrylate, bisphenol A dimethacrylate, butanediol dimethacrylate, tricyclodecane dimethanol diacrylate, pentaerythritol triacrylate, tripropylene glycol diacrylate, propoxylated neopentyl diacrylate, pentaerythritol triacrylate, ditrimethylolpropane tetraacrylate, dipentaerythritol pentaacrylate, dipentaerythritol penta/hexa-acrylate, tripropylene diacrylate, trimethylol propane ethoxylate triacrylate, trimethylol propane propoxylate triacrylate, di(trimethylolpropane) tetraacrylate, glycerol propoxylate triacrylate, pentaerythritol propoxylate triacrylate, poly(ethylene glycol) diacrylate, poly(propylene glycol) diacrylate, and tri(propylene glycol) diacrylate, and combinations thereof.

10. The beads according to claim 1, wherein the first functional monomer is selected from one or more of the group consisting of acrylic acid, methacrylic acid, 2-carboxyethyl acrylate, acrylamide, methacrylamide, allylamine, (hydroxyethyl)methacrylate, hydroxypropyl methacrylate, 4-hydroxybutyl acrylate, glycidyl methacrylate, allyl glycidyl ether, 1,2-epoxy-5-hexene, maleic anhydride, 2-hydroxyethyl methacrylate, 2-carboxyethyl acrylate oligomers, and combinations thereof.

11. The beads according to claim 1, wherein: the styrene monomer is selected from one or more of the group consisting of styrene, and a styrene derivative.

12. The beads according to claim 1, wherein the first shell further comprises a first layer of a first polymeric matrix composition and a second layer of a second polymeric matrix composition, where:

the first layer is formed from a copolymer of a styrene monomer, a crosslinking monomer; and the second layer is formed from a copolymer a styrene monomer, a crosslinking monomer and a functional monomer.

13. The beads according to claim 1, wherein the superparamagnetic $Fe_3O_4$ nanoparticles have an average diameter of from 5 to 15 nm.

14. The beads according to claim 1, wherein the $Fe_3O_4$ nanoparticles further comprise $Co_3O_4$ and/or $Mn_3O_4$ nanoparticles.

15. The superparamagnetic beads according to claim 1, wherein the combined weight of the second and third layer of the second shell accounts for from 1-30 wt % of the entire weight of each bead.

16. A method of preparing monodisperse superparamagnetic beads, having a core-shell structure, the method comprising:

(a) providing monodisperse superparamagnetic precursor beads, which comprise a core portion formed from a polystyrene polymeric matrix material, where the polystyrene polymeric matrix material encapsulates a first batch of superparamagnetic $Fe_3O_4$ nanoparticles;

a first shell portion located directly on top of the core portion and formed from a crosslinked polymeric matrix material that is formed from a styrene monomer, a crosslinking monomer and a first functional monomer that has functional groups, where the copolymeric matrix material encapsulates a second batch of superparamagnetic $Fe_3O_4$ nanoparticles; and a second shell portion located directly on top of the first shell portion, which comprises superparamagnetic $Fe_3O_4$ nanoparticles and polymeric precursor anchor points, both which are bound to the functional groups on a surface of the first shell portion; and (b) forming a functional coating layer on the monodisperse superparamagnetic precursor beads by a one-pot free radical polymerization, which:

(i) in a first step uses a bulk monomer; and (ii) in a second step uses a second functional monomer that has functional groups to form the monodisperse superparamagnetic beads, wherein the functional coating layer is bound to the first shell portion by way of the polymeric precursor anchor points.

17. The process according to claim 16, wherein the monodisperse superparamagnetic precursor beads are formed by a process that comprises:

(i) providing naked monodisperse superparamagnetic beads, which comprise a core portion formed from a polystyrene polymeric matrix material, where the polystyrene polymeric matrix material encapsulates a first batch of superparamagnetic $Fe_3O_4$ nanoparticles;

a first shell portion located directly on top of the core portion and formed from a crosslinked polymeric matrix material that is formed from a styrene monomer, a crosslinking monomer and a first functional monomer that has functional groups, where the copolymeric matrix material encapsulates a second batch of superparamagnetic $Fe_3O_4$ nanoparticles; and a second shell portion located directly on top of the first shell portion, which comprises superparamagnetic $Fe_3O_4$ nanoparticles which is bound to the functional groups on a surface of the first shell portion; and (ii) forming the monodisperse superparamagnetic precursor beads by forming polymeric precursor anchor points on the first shell portion by reacting the naked monodisperse superparamagnetic beads with an anchoring material selected from one or more of the group consisting of methacryloyl chloride, 3-ethoxyacryloyl chloride, acryloyl chloride, 4-pentenoyl chloride, methacrylic anhydride, 4-pentenoic anhydride, crotonic anhydride, valeric anhydride, 10-undecenoyl chloride, glycidol methacrylate, glycidol, allyl glycidyl ether, and combinations thereof.

18. The process according to claim 17, wherein the naked monodisperse superparamagnetic beads are formed by a process that comprises:

(ai) providing monodisperse beads, which comprise:

a core portion formed from a polystyrene polymeric matrix material; and a first shell portion located directly on top of the core portion and formed from a crosslinked polymeric matrix material that is formed from a styrene monomer, a crosslinking monomer and a first functional monomer that has functional groups; and (aii) forming the naked monodisperse superparamagnetic beads by placing the monodisperse beads into a solution that comprises a Fe(III) salt and a Fe(II) salt and adding a base.

19. The process according to claim 18, wherein the monodisperse beads are formed by a one-pot three-stage continuous process, which process comprises:

(a) in a first stage, generating a polystyrene core by dispersion polymerization of a styrene monomer with an initiator and a polymer stabilizer in a mixture of alcohol with water to form nucleated polystyrene cores;

(b) in a second stage, adding a crosslinking monomer to mixture comprising nucleated polystyrene cores; and (c) in a third stage adding a first functional monomer to the material obtained from the second stage to provide the monodisperse beads.

20. The superparamagnetic beads according to claim 1, wherein these beads are applied in IVD assays.

* * * * *